United States Patent
Blanquart et al.

(10) Patent No.: US 10,701,254 B2
(45) Date of Patent: Jun. 30, 2020

(54) CAMERA SYSTEM WITH MINIMAL AREA MONOLITHIC CMOS IMAGE SENSOR

(71) Applicant: Depuy Synthes Products, Inc., Raynham, MA (US)

(72) Inventors: Laurent Blanquart, Westlake Village, CA (US); John Richardson, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/127,015

(22) Filed: Sep. 10, 2018

(65) Prior Publication Data

US 2019/0007588 A1 Jan. 3, 2019

Related U.S. Application Data

(63) Continuation of application No. 15/284,085, filed on Oct. 3, 2016, now Pat. No. 10,075,626, which is a
(Continued)

(51) Int. Cl.
| | |
|---|---|
| H04N 5/225 | (2006.01) |
| A61B 1/00 | (2006.01) |
| A61B 1/05 | (2006.01) |
| H04N 7/18 | (2006.01) |
| A61B 1/313 | (2006.01) |

(Continued)

(52) U.S. Cl.
CPC ....... *H04N 5/2256* (2013.01); *A61B 1/00009* (2013.01); *A61B 1/051* (2013.01); *A61B 1/317* (2013.01); *A61B 1/3132* (2013.01); *H04N 5/2352* (2013.01); *H04N 5/374* (2013.01); *H04N 5/378* (2013.01); *H04N 7/18* (2013.01); *H04N 7/181* (2013.01); *H04N 2005/2255* (2013.01)

(58) Field of Classification Search
CPC ...... H04N 5/2256; H04N 7/181; H04N 5/378; H04N 5/374; H04N 5/2352; H04N 7/18; H04N 2005/2255; A61B 1/317; A61B 1/3132; A61B 1/051; A61B 1/00009; A61B 1/05
See application file for complete search history.

(56) References Cited

U.S. PATENT DOCUMENTS

| | | |
|---|---|---|
| 3,796,220 A | 3/1974 | Bredemeier |
| 3,858,577 A | 1/1975 | Bass et al. |
| (Continued) | | |

FOREIGN PATENT DOCUMENTS

| | | |
|---|---|---|
| AU | 2012253253 B2 | 11/2012 |
| AU | 2012253261 | 6/2016 |
| (Continued) | | |

OTHER PUBLICATIONS

H.Kurino et al., Intelligent image sensor chip with three dimensional structure, Technical Digest, International Electron Devices Meeting 1999, Dec. 5, 1999, pp. 879-882.

*Primary Examiner* — James M Pontius
(74) *Attorney, Agent, or Firm* — Terrence J. Edwards; TechLaw Ventures, PLLC

(57) ABSTRACT

The disclosure extends to methods, systems, and computer program products for digitally imaging with area limited image sensors, such as within a lumen of an endoscope.

20 Claims, 15 Drawing Sheets

Related U.S. Application Data continuation of application No. 13/952,550, filed on Jul. 26, 2013, now Pat. No. 9,462,234.

(60) Provisional application No. 61/790,590, filed on Mar. 15, 2013, provisional application No. 61/676,289, filed on Jul. 26, 2012.

(51) Int. Cl.
*A61B 1/317* (2006.01)
*H04N 5/235* (2006.01)
*H04N 5/374* (2011.01)
*H04N 5/378* (2011.01)

(56) References Cited

U.S. PATENT DOCUMENTS

| | | |
|---|---|---|
| 4,011,403 A | 3/1977 | Epstein et al. |
| 4,153,356 A | 5/1979 | Hama |
| 4,350,150 A | 9/1982 | Kubota et al. |
| 4,363,963 A | 12/1982 | Ando |
| 4,429,686 A | 2/1984 | Hosoda |
| 4,433,675 A | 2/1984 | Konoshima |
| 4,436,095 A | 3/1984 | Kruger |
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkie et al. |
| 4,740,837 A | 4/1988 | Yanagisawa et al. |
| 4,741,327 A | 5/1988 | Yabe |
| 4,745,471 A | 5/1988 | Takamura et al. |
| 4,773,396 A | 9/1988 | Okazaki |
| 4,786,965 A | 11/1988 | Yabe |
| 4,800,424 A | 1/1989 | Noguchi |
| 4,831,444 A | 5/1989 | Kato |
| 4,832,003 A | 5/1989 | Yabe |
| 4,845,555 A | 7/1989 | Yabe et al. |
| 4,853,772 A | 8/1989 | Kikuchi |
| 4,866,526 A | 9/1989 | Ams et al. |
| 4,888,639 A | 12/1989 | Yabe et al. |
| 4,918,521 A | 4/1990 | Yabe et al. |
| 4,938,205 A | 7/1990 | Nudelman |
| 4,942,473 A | 7/1990 | Zeevi et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,016,975 A | 5/1991 | Sasaki et al. |
| 5,021,888 A | 6/1991 | Kondou et al. |
| 5,042,915 A | 8/1991 | Akutsu et al. |
| 5,065,444 A | 11/1991 | Garber |
| RE33,854 E | 3/1992 | Adair |
| 5,103,497 A | 4/1992 | Hicks |
| 5,111,804 A | 5/1992 | Funakoshi |
| 5,115,309 A | 5/1992 | Hang |
| 5,133,035 A | 7/1992 | Hicks |
| 5,168,361 A | 12/1992 | Hackmann |
| 5,168,863 A | 12/1992 | Kurtzer |
| 5,187,572 A | 2/1993 | Nakamura et al. |
| 5,188,094 A | 2/1993 | Adair |
| 5,196,938 A | 3/1993 | Blessinger |
| 5,200,838 A | 4/1993 | Nudelman et al. |
| 5,220,198 A | 6/1993 | Tsuji |
| 5,227,662 A | 7/1993 | Ohno et al. |
| 5,228,430 A | 7/1993 | Sakamoto |
| 5,237,403 A | 8/1993 | Sugimoto et al. |
| 5,241,170 A | 8/1993 | Field, Jr. et al. |
| 5,277,172 A | 1/1994 | Sugimoto |
| 5,289,555 A | 2/1994 | Sanso |
| 5,307,804 A | 5/1994 | Bonnet |
| 5,313,306 A | 5/1994 | Kuban et al. |
| 5,325,847 A | 7/1994 | Matsuno |
| 5,339,275 A | 8/1994 | Hyatt |
| 5,381,784 A | 1/1995 | Adair |
| 5,400,267 A | 3/1995 | Denen et al. |
| 5,402,768 A | 4/1995 | Adair |
| 5,411,020 A | 5/1995 | Ito |
| 5,427,087 A | 6/1995 | Ito et al. |
| 5,454,366 A | 10/1995 | Ito et al. |
| 5,461,425 A | 10/1995 | Fowler et al. |
| 5,471,515 A | 11/1995 | Fossum et al. |
| 5,489,801 A | 2/1996 | Blish, II |
| 5,494,483 A | 2/1996 | Adair |
| 5,522,006 A | 5/1996 | Takeuchi et al. |
| 5,523,786 A | 6/1996 | Parulski |
| 5,550,595 A | 8/1996 | Hannah |
| 5,576,781 A | 11/1996 | Deleeuw |
| 5,594,282 A | 1/1997 | Otsuki |
| 5,594,497 A | 1/1997 | Ahern et al. |
| 5,614,763 A | 3/1997 | Womack |
| 5,665,959 A | 9/1997 | Fossum et al. |
| 5,734,418 A | 3/1998 | Danna |
| 5,748,234 A | 5/1998 | Lippincott |
| 5,754,313 A | 5/1998 | Pelchy et al. |
| 5,757,075 A | 5/1998 | Kitaoka |
| 5,784,099 A | 7/1998 | Lippincott |
| 5,787,298 A | 7/1998 | Broedner et al. |
| 5,841,126 A | 11/1998 | Fossum et al. |
| 5,857,963 A | 1/1999 | Pelchy et al. |
| 5,879,289 A | 3/1999 | Yarush et al. |
| 5,887,049 A | 3/1999 | Fossum |
| 5,896,166 A | 4/1999 | D'Alfonso et al. |
| 5,907,178 A | 5/1999 | Baker et al. |
| 5,929,901 A | 7/1999 | Adair et al. |
| 5,949,483 A | 9/1999 | Fossum et al. |
| 5,986,693 A | 11/1999 | Adair et al. |
| 5,990,506 A | 11/1999 | Fossum et al. |
| 6,005,619 A | 12/1999 | Fossum |
| 6,018,364 A * | 1/2000 | Mangelsdorf ........ H04N 5/3575 348/241 |
| 6,021,172 A | 2/2000 | Fossum et al. |
| 6,023,315 A | 2/2000 | Harrold et al. |
| 6,027,955 A | 2/2000 | Lee et al. |
| 6,028,330 A | 2/2000 | Lee et al. |
| 6,043,839 A | 3/2000 | Adair et al. |
| 6,059,776 A | 5/2000 | Gatto |
| 6,059,793 A | 5/2000 | Pagedas |
| 6,073,043 A | 6/2000 | Schneider |
| 6,096,573 A | 8/2000 | Chen |
| 6,101,232 A | 8/2000 | Fossum et al. |
| 6,118,142 A | 9/2000 | Chen et al. |
| 6,139,489 A | 10/2000 | Wampler et al. |
| 6,142,930 A | 11/2000 | Ito et al. |
| 6,144,542 A | 11/2000 | Ker et al. |
| 6,166,367 A | 12/2000 | Cho |
| 6,166,768 A | 12/2000 | Fossum et al. |
| 6,180,969 B1 | 1/2001 | Yang et al. |
| 6,184,055 B1 | 2/2001 | Yang et al. |
| 6,194,260 B1 | 2/2001 | Chien et al. |
| 6,198,087 B1 | 3/2001 | Boon |
| 6,207,984 B1 | 3/2001 | Chang |
| 6,211,904 B1 | 4/2001 | Adair et al. |
| 6,215,517 B1 | 4/2001 | Takahashi et al. |
| 6,239,456 B1 | 5/2001 | Berezin et al. |
| 6,242,277 B1 | 6/2001 | Lin et al. |
| 6,255,681 B1 | 7/2001 | Pan |
| 6,272,269 B1 | 8/2001 | Naum |
| 6,275,255 B1 | 8/2001 | Adair et al. |
| 6,294,775 B1 | 9/2001 | Seibel et al. |
| 6,303,421 B1 | 10/2001 | Chang |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,327,493 B1 | 12/2001 | Ozawa et al. |
| 6,331,156 B1 | 12/2001 | Haefele et al. |
| 6,333,205 B1 | 12/2001 | Rhodes |
| 6,369,812 B1 | 4/2002 | Iyriboz et al. |
| 6,387,043 B1 | 5/2002 | Yoon |
| 6,388,243 B1 | 5/2002 | Berezin et al. |
| 6,389,205 B1 | 5/2002 | Muckner et al. |
| 6,390,972 B1 | 5/2002 | Speier et al. |
| 6,400,824 B1 | 6/2002 | Mansoorian et al. |

(56) References Cited

U.S. PATENT DOCUMENTS

| | | |
|---|---|---|
| 6,404,048 B2 | 6/2002 | Akram |
| 6,410,377 B1 | 6/2002 | Hwang et al. |
| 6,416,463 B1 | 7/2002 | Tsuzuki et al. |
| 6,419,626 B1 | 7/2002 | Yoon |
| 6,419,627 B1 | 7/2002 | Ben Nun |
| 6,424,369 B1 | 7/2002 | Adair et al. |
| 6,436,032 B1 | 8/2002 | Eto et al. |
| 6,441,482 B1 | 8/2002 | Foster |
| 6,452,626 B1 | 9/2002 | Adair et al. |
| 6,456,326 B2 | 9/2002 | Fossum et al. |
| 6,469,739 B1 | 10/2002 | Bechtel et al. |
| 6,485,414 B1 | 11/2002 | Neuberger |
| 6,512,280 B2 | 1/2003 | Chen et al. |
| 6,515,321 B1 | 2/2003 | Jwo |
| 6,549,235 B1 | 4/2003 | Fossum et al. |
| 6,555,842 B1 | 4/2003 | Fossum et al. |
| 6,570,617 B2 | 5/2003 | Fossum et al. |
| 6,588,884 B1 | 7/2003 | Furlani et al. |
| 6,606,122 B1 | 8/2003 | Shaw et al. |
| 6,610,557 B2 | 8/2003 | Lee et al. |
| 6,627,474 B2 | 9/2003 | Barna et al. |
| 6,659,940 B2 | 12/2003 | Adler |
| 6,665,013 B1 | 12/2003 | Fossum et al. |
| 6,690,466 B2 | 2/2004 | Miller et al. |
| 6,692,431 B2 | 2/2004 | Kazakevich |
| 6,704,049 B1 | 3/2004 | Fossum |
| 6,720,810 B1 | 4/2004 | New |
| 6,726,620 B2 | 4/2004 | Shibata et al. |
| 6,730,900 B2 | 5/2004 | Hsish et al. |
| 6,740,870 B1 | 5/2004 | Doudoumopoulos |
| 6,744,068 B2 | 6/2004 | Fossum et al. |
| 6,773,392 B2 | 8/2004 | Kikuchi et al. |
| 6,784,940 B1 | 8/2004 | Takazawa et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,812,949 B1 | 11/2004 | Switzer et al. |
| 6,838,653 B2 | 1/2005 | Campbell et al. |
| 6,838,716 B2 | 1/2005 | Asada et al. |
| 6,856,712 B2 | 1/2005 | Fauver et al. |
| 6,862,036 B2 | 3/2005 | Adair et al. |
| 6,879,340 B1 | 4/2005 | Chevallier |
| 6,897,082 B2 | 5/2005 | Rhodes et al. |
| 6,899,675 B2 | 5/2005 | Cline et al. |
| 6,921,920 B2 | 7/2005 | Kazakevich |
| 6,943,838 B2 | 9/2005 | Fossum et al. |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,976,954 B2 | 12/2005 | Takahashi |
| 6,977,733 B2 | 12/2005 | Denk et al. |
| 6,982,740 B2 | 1/2006 | Adair et al. |
| 6,982,742 B2 | 1/2006 | Adair et al. |
| 6,997,871 B2 | 2/2006 | Sonnenschein et al. |
| 6,999,118 B2 | 2/2006 | Suzuki |
| 7,002,231 B2 | 2/2006 | Rhodes et al. |
| 7,002,621 B2 | 2/2006 | Adair et al. |
| 7,009,634 B2 | 3/2006 | Iddan et al. |
| 7,009,646 B1 | 3/2006 | Fossum et al. |
| 7,018,331 B2 | 3/2006 | Chang et al. |
| 7,027,092 B2 | 4/2006 | Altree |
| 7,030,904 B2 | 4/2006 | Adair et al. |
| 7,037,259 B2 | 5/2006 | Hakamata et al. |
| 7,061,117 B2 | 6/2006 | Yang et al. |
| 7,068,878 B2 | 6/2006 | Crossman-Bosworth et al. |
| 7,070,560 B2 | 7/2006 | Takahashi |
| 7,071,979 B1 | 7/2006 | Ohtani et al. |
| 7,088,398 B1 | 8/2006 | Wolf et al. |
| 7,102,682 B2 | 9/2006 | Baer |
| 7,105,371 B2 | 9/2006 | Fossum et al. |
| 7,106,367 B2 | 9/2006 | Sarwari |
| 7,106,377 B2 | 9/2006 | Bean et al. |
| 7,115,091 B2 | 10/2006 | Root et al. |
| 7,129,108 B2 | 10/2006 | Jang |
| 7,151,568 B2 | 12/2006 | Kawachi et al. |
| 7,183,129 B2 | 2/2007 | Lee |
| 7,184,084 B2 | 2/2007 | Glenn |
| 7,189,226 B2 | 3/2007 | Auld et al. |
| 7,193,519 B2 | 3/2007 | Root et al. |
| 7,202,899 B2 | 4/2007 | Lin et al. |
| 7,217,967 B2 | 5/2007 | Han |
| 7,227,469 B2 | 6/2007 | Varner et al. |
| 7,230,247 B2 | 6/2007 | Shibayama |
| 7,230,615 B2 | 6/2007 | Wang et al. |
| 7,232,712 B2 | 6/2007 | Han |
| 7,244,920 B2 | 7/2007 | Kim et al. |
| 7,250,594 B2 | 7/2007 | Lin et al. |
| 7,258,546 B2 | 8/2007 | Beier et al. |
| 7,258,663 B2 | 8/2007 | Doguchi et al. |
| 7,261,687 B2 | 8/2007 | Yang |
| 7,273,452 B2 | 9/2007 | Barbato et al. |
| 7,274,390 B2 | 9/2007 | Sevat et al. |
| 7,276,785 B2 | 10/2007 | Bauer et al. |
| 7,280,139 B2 | 10/2007 | Pahr et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 11/2007 | Johnston |
| 7,317,955 B2 | 1/2008 | McGreevy |
| 7,319,478 B2 | 1/2008 | Dolt et al. |
| 7,331,523 B2 | 2/2008 | Meier et al. |
| 7,338,832 B2 | 3/2008 | Park et al. |
| 7,339,982 B2 | 3/2008 | Wood, Jr. |
| 7,354,841 B2 | 4/2008 | Jeon |
| 7,365,768 B1 | 4/2008 | Ono et al. |
| 7,368,771 B2 | 5/2008 | Roh et al. |
| 7,369,166 B2 | 5/2008 | Fossum et al. |
| 7,369,176 B2 | 5/2008 | Sonnenschein et al. |
| 7,386,084 B2 | 6/2008 | Yin |
| 7,391,013 B2 | 6/2008 | Johnston et al. |
| 7,397,076 B2 | 7/2008 | Jang |
| 7,402,811 B2 | 7/2008 | Hatanaka et al. |
| 7,443,296 B2 | 10/2008 | Mezhinsky et al. |
| 7,470,893 B2 | 12/2008 | Suzuki et al. |
| 7,488,637 B2 | 2/2009 | Kim |
| 7,511,257 B2 | 3/2009 | Lee et al. |
| 7,517,351 B2 | 4/2009 | Culp et al. |
| 7,522,341 B2 | 4/2009 | Mouli |
| 7,525,168 B2 | 4/2009 | Hsieh |
| 7,534,645 B2 | 5/2009 | Choi |
| 7,535,037 B2 | 5/2009 | Lyu |
| 7,540,645 B2 | 6/2009 | Kazakevich |
| 7,542,069 B2 | 6/2009 | Tashiro |
| 7,544,163 B2 | 6/2009 | MacKinnon et al. |
| 7,545,434 B2 | 6/2009 | Bean et al. |
| 7,551,059 B2 | 6/2009 | Farrier |
| 7,564,935 B2 | 7/2009 | Suzuki |
| 7,567,291 B2 | 7/2009 | Bechtel et al. |
| 7,568,619 B2 | 8/2009 | Todd et al. |
| 7,573,516 B2 | 8/2009 | Krymski et al. |
| 7,578,786 B2 | 8/2009 | Boulais et al. |
| 7,583,872 B2 | 9/2009 | Seibel et al. |
| 7,589,349 B2 | 9/2009 | Hong |
| 7,595,210 B2 | 9/2009 | Shim |
| 7,598,686 B2 | 10/2009 | Lys et al. |
| 7,599,439 B2 | 10/2009 | Lavelle et al. |
| 7,605,016 B2 | 10/2009 | Min |
| 7,608,874 B2 | 10/2009 | Lee et al. |
| 7,612,318 B2 | 11/2009 | Jeon |
| 7,615,808 B2 | 11/2009 | Pain et al. |
| 7,615,838 B2 | 11/2009 | Kim |
| 7,616,986 B2 | 11/2009 | Seibel et al. |
| 7,630,008 B2 | 12/2009 | Sarwari |
| 7,646,407 B2 | 1/2010 | Fossum et al. |
| 7,663,115 B2 | 2/2010 | Korthout et al. |
| 7,744,528 B2 | 6/2010 | Wallace et al. |
| 7,749,799 B2 | 7/2010 | Pain |
| 7,768,562 B2 | 8/2010 | Boemler |
| 7,794,394 B2 | 9/2010 | Frangioni |
| 7,795,650 B2 | 9/2010 | Eminoglu et al. |
| 7,800,192 B2 | 9/2010 | Venezia et al. |
| 7,801,584 B2 | 9/2010 | Iddan et al. |
| 7,812,801 B2 * | 10/2010 | Takane .......... H04N 5/2351 345/87 |

(56) References Cited

U.S. PATENT DOCUMENTS

| | | | |
|---|---|---|---|
| 7,830,434 B2 | 11/2010 | Li et al. |
| 7,868,283 B2 | 1/2011 | Mabuchi |
| 7,871,373 B2 | 1/2011 | Yamada |
| 7,880,662 B2 | 2/2011 | Bogaerts |
| 7,901,974 B2 | 3/2011 | Venezia et al. |
| 7,914,447 B2 | 3/2011 | Kanai |
| 7,916,193 B2 | 3/2011 | Fossum |
| 7,923,763 B2 | 4/2011 | Lauxtermann |
| 7,935,050 B2 | 5/2011 | Launava et al. |
| 7,936,394 B2 | 5/2011 | Wu |
| 7,944,566 B2 | 5/2011 | Xie |
| 7,952,096 B2 | 5/2011 | Rhodes |
| 7,973,342 B2 | 7/2011 | Jeon |
| 7,995,123 B2 | 8/2011 | Lee et al. |
| 8,089,542 B2 | 1/2012 | Chevallier |
| 8,100,826 B2 | 1/2012 | MacKinnon et al. |
| 8,101,903 B2 | 1/2012 | Mokhnatyuk |
| 8,154,055 B2 | 4/2012 | Ha |
| 8,159,584 B2 | 4/2012 | Iwabuchi et al. |
| 8,164,659 B2 * | 4/2012 | Mori ............... A61B 1/00009 348/245 |
| 8,193,542 B2 | 6/2012 | Machara |
| 8,212,884 B2 | 7/2012 | Seibel et al. |
| 8,300,111 B2 | 10/2012 | Iwane |
| 8,317,689 B1 | 11/2012 | Remijan et al. |
| 8,339,482 B2 * | 12/2012 | Okado ............... H04N 5/3595 348/241 |
| 8,382,662 B2 | 2/2013 | Soper et al. |
| 8,384,814 B2 | 2/2013 | Chevallier |
| 8,396,535 B2 | 3/2013 | Wang et al. |
| 8,405,748 B2 | 3/2013 | Mao et al. |
| 8,419,632 B2 * | 4/2013 | Kimoto ............. A61B 1/00036 600/180 |
| 8,423,110 B2 | 4/2013 | Barbato et al. |
| 8,426,096 B2 | 4/2013 | Maezawa |
| 8,471,938 B2 | 6/2013 | Altice, Jr. et al. |
| 8,476,575 B2 | 7/2013 | Mokhnatyuk |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,582,011 B2 | 11/2013 | Dosluoglu |
| 8,602,971 B2 | 12/2013 | Farr |
| 8,614,754 B2 | 12/2013 | Fossum |
| 8,625,016 B2 | 1/2014 | Fossum et al. |
| 8,629,023 B2 | 1/2014 | Lee |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,733,660 B2 | 5/2014 | Wang et al. |
| 8,754,358 B2 | 6/2014 | Chou et al. |
| 8,797,434 B2 | 8/2014 | Lee et al. |
| 8,830,340 B2 | 9/2014 | Burt et al. |
| 8,836,834 B2 | 9/2014 | Hashimoto et al. |
| 8,854,517 B2 | 10/2014 | Honda et al. |
| 8,858,425 B2 | 10/2014 | Farr et al. |
| 8,885,034 B2 | 11/2014 | Adair et al. |
| 8,896,730 B2 | 11/2014 | Fossum |
| 8,952,312 B2 | 2/2015 | Blanquart et al. |
| 9,066,677 B2 | 6/2015 | Seto |
| 9,123,602 B2 | 9/2015 | Blanquart |
| 9,153,609 B2 | 10/2015 | Blanquart |
| 9,343,489 B2 | 5/2016 | Blanquart et al. |
| 9,462,234 B2 | 10/2016 | Blanquart et al. |
| 9,763,566 B2 | 9/2017 | Blanquart |
| 9,993,143 B2 * | 6/2018 | Mitsuhashi ............. A61B 1/045 |
| 2001/0016804 A1 | 8/2001 | Cunningham et al. |
| 2001/0019361 A1 | 9/2001 | Savoye |
| 2001/0030744 A1 | 10/2001 | Chang |
| 2001/0041825 A1 | 11/2001 | Shibata et al. |
| 2001/0052930 A1 | 12/2001 | Adair et al. |
| 2002/0011809 A1 | 1/2002 | Hartge et al. |
| 2002/0017611 A1 | 2/2002 | Tashiro et al. |
| 2002/0044207 A1 | 4/2002 | Dielhof et al. |
| 2002/0067408 A1 | 6/2002 | Adair et al. |
| 2002/0080248 A1 | 6/2002 | Adair et al. |
| 2002/0158986 A1 | 10/2002 | Baer |
| 2002/0163578 A1 | 11/2002 | Adair et al. |
| 2002/0180867 A1 | 12/2002 | Adair et al. |
| 2003/0007087 A1 | 1/2003 | Hakamata et al. |
| 2003/0007686 A1 | 1/2003 | Roever |
| 2003/0043264 A1 | 3/2003 | Furuya et al. |
| 2003/0052983 A1 | 3/2003 | Altree |
| 2003/0107664 A1 | 6/2003 | Suzuki |
| 2003/0146994 A1 | 8/2003 | Kokubun |
| 2003/0163029 A1 | 8/2003 | Sonnenschein et al. |
| 2003/0187586 A1 | 10/2003 | Katzenmaier et al. |
| 2003/0189663 A1 | 10/2003 | Dolt et al. |
| 2003/0218120 A1 | 11/2003 | Shibayama |
| 2004/0010196 A1 | 1/2004 | Wang et al. |
| 2004/0036010 A1 | 2/2004 | Hsieh et al. |
| 2004/0049215 A1 | 3/2004 | Snow et al. |
| 2004/0073086 A1 | 4/2004 | Abe |
| 2004/0078494 A1 | 4/2004 | Lennox et al. |
| 2004/0082833 A1 | 4/2004 | Adler et al. |
| 2004/0095495 A1 | 5/2004 | Inokuma et al. |
| 2004/0111012 A1 | 6/2004 | Whitman |
| 2004/0169771 A1 | 9/2004 | Washington et al. |
| 2004/0170712 A1 | 9/2004 | Sadek El Mogy |
| 2004/0249267 A1 | 12/2004 | Gilboa |
| 2005/0009982 A1 | 1/2005 | Inagaki et al. |
| 2005/0027164 A1 | 2/2005 | Barbato et al. |
| 2005/0038322 A1 | 2/2005 | Banik |
| 2005/0075538 A1 | 4/2005 | Banik et al. |
| 2005/0083420 A1 * | 4/2005 | Koseki ............... H04N 5/378 348/294 |
| 2005/0131279 A1 | 6/2005 | Boulais et al. |
| 2005/0148819 A1 | 7/2005 | Noguchi et al. |
| 2005/0151866 A1 | 7/2005 | Ando et al. |
| 2005/0168941 A1 | 8/2005 | Sokol et al. |
| 2005/0174428 A1 | 8/2005 | Abe |
| 2005/0206755 A1 | 9/2005 | Yokoyama et al. |
| 2005/0222499 A1 | 10/2005 | Banik et al. |
| 2005/0231591 A1 | 10/2005 | Abe |
| 2005/0234302 A1 | 10/2005 | MacKinnon et al. |
| 2005/0237412 A1 | 10/2005 | Shiohara et al. |
| 2005/0288546 A1 | 12/2005 | Sonnenschein et al. |
| 2006/0007507 A1 | 1/2006 | Inaba et al. |
| 2006/0022234 A1 | 2/2006 | Adair et al. |
| 2006/0023109 A1 | 2/2006 | Mabuchi et al. |
| 2006/0035415 A1 | 2/2006 | Wood et al. |
| 2006/0061668 A1 * | 3/2006 | Ise ............... H04N 5/3575 348/222.1 |
| 2006/0069314 A1 | 3/2006 | Farr |
| 2006/0074289 A1 | 4/2006 | Adler et al. |
| 2006/0164533 A1 | 7/2006 | Hsieh et al. |
| 2006/0181627 A1 | 8/2006 | Farrier |
| 2006/0221230 A1 | 10/2006 | Dutta et al. |
| 2006/0249765 A1 | 11/2006 | Hsieh |
| 2006/0250513 A1 | 11/2006 | Yamamoto et al. |
| 2006/0293563 A1 | 12/2006 | Banik et al. |
| 2006/0293565 A1 | 12/2006 | Uchimura et al. |
| 2007/0002134 A1 | 1/2007 | Ishihara et al. |
| 2007/0010712 A1 | 1/2007 | Negishi |
| 2007/0013793 A1 * | 1/2007 | Konda ............... G06K 9/00798 348/241 |
| 2007/0030262 A1 | 2/2007 | Ambo et al. |
| 2007/0030345 A1 | 2/2007 | Amling et al. |
| 2007/0046803 A1 | 3/2007 | Ahn |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0129601 A1 | 6/2007 | Johnston et al. |
| 2007/0138375 A1 | 6/2007 | Lee et al. |
| 2007/0153337 A1 | 7/2007 | Kim |
| 2007/0159526 A1 | 7/2007 | Abe |
| 2007/0165120 A1 * | 7/2007 | Takane ............... H04N 5/2351 348/248 |
| 2007/0182842 A1 | 8/2007 | Sonnenschein et al. |
| 2007/0185549 A1 | 8/2007 | Zdeblick |
| 2007/0187703 A1 | 8/2007 | Erchak |

(56) References Cited

U.S. PATENT DOCUMENTS

| | | |
|---|---|---|
| 2007/0197873 A1 | 8/2007 | Birnkrant |
| 2007/0225556 A1 | 9/2007 | Ortiz et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0279486 A1 | 12/2007 | Bayer et al. |
| 2007/0297190 A1 | 12/2007 | Ng |
| 2008/0021271 A1 | 1/2008 | Pasero et al. |
| 2008/0042046 A1 | 2/2008 | Mabuchi |
| 2008/0045800 A2 | 2/2008 | Farr |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0158348 A1 | 7/2008 | Karpen et al. |
| 2008/0165360 A1 | 7/2008 | Johnston |
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0239124 A1 | 10/2008 | Mori et al. |
| 2008/0249369 A1 | 10/2008 | Seibel et al. |
| 2008/0255416 A1 | 10/2008 | Gilboa |
| 2008/0258042 A1 | 10/2008 | Krymski |
| 2008/0287798 A1 | 11/2008 | Lee et al. |
| 2008/0291290 A1 | 11/2008 | Sonoda et al. |
| 2008/0291506 A1* | 11/2008 | Mizuta .............. H01L 27/14623 358/465 |
| 2008/0309810 A1 | 12/2008 | Smith et al. |
| 2008/0316319 A1 | 12/2008 | Nomoto |
| 2009/0012361 A1 | 1/2009 | MacKinnon et al. |
| 2009/0012368 A1 | 1/2009 | Banik |
| 2009/0015301 A1 | 1/2009 | Marchesini et al. |
| 2009/0021588 A1 | 1/2009 | Border et al. |
| 2009/0021619 A1* | 1/2009 | Kasuga .................. H04N 5/357 348/300 |
| 2009/0021628 A1 | 1/2009 | Tamakoshi |
| 2009/0040783 A1 | 2/2009 | Krupa et al. |
| 2009/0054908 A1 | 2/2009 | Zand et al. |
| 2009/0062656 A1 | 3/2009 | Hyuga |
| 2009/0074265 A1 | 3/2009 | Huang et al. |
| 2009/0076329 A1 | 3/2009 | Su et al. |
| 2009/0082630 A1 | 3/2009 | Tulley |
| 2009/0091641 A1 | 4/2009 | Hattori |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0154886 A1 | 6/2009 | Lewis et al. |
| 2009/0160976 A1 | 6/2009 | Chen et al. |
| 2009/0160979 A1 | 6/2009 | Xu et al. |
| 2009/0167908 A1* | 7/2009 | Mori .................. A61B 1/00009 348/251 |
| 2009/0173974 A1 | 7/2009 | Shah et al. |
| 2009/0184349 A1 | 7/2009 | Dungan |
| 2009/0186780 A1 | 7/2009 | Lee et al. |
| 2009/0192390 A1 | 7/2009 | Berguer et al. |
| 2009/0200624 A1 | 8/2009 | Dai et al. |
| 2009/0203966 A1 | 8/2009 | Mizuyoshi |
| 2009/0208143 A1 | 8/2009 | Yoon et al. |
| 2009/0212397 A1 | 8/2009 | Tuttle |
| 2009/0216080 A1 | 8/2009 | Nakamura |
| 2009/0224136 A1* | 9/2009 | Ikegami ................ H05B 45/10 250/205 |
| 2009/0225548 A1 | 9/2009 | Narita |
| 2009/0227847 A1 | 9/2009 | Tepper et al. |
| 2009/0230287 A1 | 9/2009 | Anderson et al. |
| 2009/0236500 A1 | 9/2009 | Shah et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0292168 A1 | 11/2009 | Farr |
| 2009/0306478 A1 | 12/2009 | Mizuyoshi |
| 2009/0316116 A1 | 12/2009 | Melville et al. |
| 2009/0322911 A1 | 12/2009 | Blanquart |
| 2009/0322912 A1 | 12/2009 | Blanquart |
| 2010/0026824 A1 | 2/2010 | Chen |
| 2010/0039156 A1 | 2/2010 | Yamaguchi |
| 2010/0049180 A1 | 2/2010 | Wells et al. |
| 2010/0059802 A1 | 3/2010 | Chen |
| 2010/0118932 A1 | 5/2010 | Luo et al. |
| 2010/0121142 A1 | 5/2010 | OuYang et al. |
| 2010/0134662 A1 | 6/2010 | Bub |
| 2010/0137684 A1 | 6/2010 | Shibasaki et al. |
| 2010/0157037 A1 | 6/2010 | Iketani et al. |
| 2010/0157039 A1 | 6/2010 | Sugai |
| 2010/0157117 A1 | 6/2010 | Wang |
| 2010/0171429 A1 | 7/2010 | Garcia et al. |
| 2010/0178722 A1 | 7/2010 | de Graff et al. |
| 2010/0182446 A1 | 7/2010 | Matsubayashi |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2010/0245647 A1 | 9/2010 | Honda et al. |
| 2010/0276572 A1 | 11/2010 | Iwabuchi et al. |
| 2010/0290100 A1 | 11/2010 | Karasawa |
| 2010/0295978 A1 | 11/2010 | Nakamura et al. |
| 2010/0305406 A1 | 12/2010 | Braun et al. |
| 2010/0315333 A1 | 12/2010 | Hsu |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0050874 A1 | 3/2011 | Reshef et al. |
| 2011/0050969 A1 | 3/2011 | Nishihara |
| 2011/0055447 A1 | 3/2011 | Costa |
| 2011/0063428 A1 | 3/2011 | Sonnenschein et al. |
| 2011/0449591 | 3/2011 | Nakatani et al. |
| 2011/0115663 A1 | 5/2011 | Bogaerts |
| 2011/0121654 A1 | 5/2011 | Recker et al. |
| 2011/0128408 A1 | 6/2011 | Ishigaki et al. |
| 2011/0181709 A1 | 7/2011 | Wright et al. |
| 2011/0181840 A1 | 7/2011 | Cobb |
| 2011/0184239 A1 | 7/2011 | Wright et al. |
| 2011/0184243 A1 | 7/2011 | Wright et al. |
| 2011/0208004 A1 | 8/2011 | Feingold et al. |
| 2011/0218399 A1* | 9/2011 | Kimoto .............. A61B 1/00036 600/109 |
| 2011/0228790 A1 | 9/2011 | Martin de Nicolas |
| 2011/0237882 A1 | 9/2011 | Saito |
| 2011/0237884 A1 | 9/2011 | Saito |
| 2011/0238977 A1 | 9/2011 | Talbert et al. |
| 2011/0242300 A1 | 10/2011 | Shiohara et al. |
| 2011/0245605 A1 | 10/2011 | Jacobsen et al. |
| 2011/0263941 A1 | 10/2011 | Wright et al. |
| 2011/0279679 A1 | 11/2011 | Samuel et al. |
| 2011/0288374 A1 | 11/2011 | Hadani et al. |
| 2011/0292258 A1 | 12/2011 | Adler et al. |
| 2011/0295061 A1 | 12/2011 | Haramaty et al. |
| 2011/0298908 A1 | 12/2011 | Murakami |
| 2011/0304757 A1* | 12/2011 | Egawa .................. H04N 5/355 348/300 |
| 2012/0004508 A1 | 1/2012 | McDowall et al. |
| 2012/0006973 A1* | 1/2012 | Storm .................. H04N 5/3575 250/208.1 |
| 2012/0014563 A1 | 1/2012 | Bendall |
| 2012/0029279 A1 | 2/2012 | Kucklick |
| 2012/0035419 A1 | 2/2012 | Ashida et al. |
| 2012/0035434 A1 | 2/2012 | Ferren et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0071720 A1 | 3/2012 | Banik et al. |
| 2012/0078052 A1 | 3/2012 | Cheng |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0147229 A1 | 6/2012 | Shah et al. |
| 2012/0188623 A1* | 7/2012 | Inoue .................. G02B 26/101 359/197.1 |
| 2012/0265196 A1 | 10/2012 | Turner et al. |

(56) References Cited

U.S. PATENT DOCUMENTS

| | | |
|---|---|---|
| 2012/0293699 A1 | 11/2012 | Blanquart et al. |
| 2012/0307030 A1 | 12/2012 | Blanquart |
| 2013/0010166 A1 | 1/2013 | Morisaki et al. |
| 2013/0126707 A1 | 5/2013 | Blanquart |
| 2013/0126708 A1 | 5/2013 | Blanquart |
| 2013/0126709 A1 | 5/2013 | Blanquart |
| 2013/0144122 A1 | 6/2013 | Adair et al. |
| 2013/0158346 A1 | 6/2013 | Soper et al. |
| 2013/0176409 A1 | 7/2013 | Kotani et al. |
| 2013/0222165 A1 | 8/2013 | David et al. |
| 2013/0242069 A1 | 9/2013 | Kobayashi |
| 2013/0264465 A1 | 10/2013 | Dai et al. |
| 2013/0292854 A1 | 11/2013 | Lua et al. |
| 2013/0300837 A1 | 11/2013 | DiCarlo et al. |
| 2014/0052004 A1 | 2/2014 | D'Alfonso et al. |
| 2014/0073852 A1 | 3/2014 | Banik et al. |
| 2014/0104466 A1 | 4/2014 | Fossum |
| 2014/0160259 A1 | 6/2014 | Blanquart et al. |
| 2014/0175591 A1 | 6/2014 | Tian et al. |
| 2014/0198240 A1 | 7/2014 | Rhoads |
| 2014/0203084 A1 | 7/2014 | Wang |
| 2014/0217268 A1 | 8/2014 | Schleipen et al. |
| 2014/0240568 A1* | 8/2014 | Yamagata ............ H04N 5/378 348/308 |
| 2014/0267851 A1 | 9/2014 | Rhoads |
| 2014/0275783 A1 | 9/2014 | Blanquart |
| 2014/0285645 A1 | 9/2014 | Blanquart et al. |
| 2014/0300698 A1 | 10/2014 | Wany |
| 2014/0354788 A1 | 12/2014 | Yano |
| 2014/0364689 A1 | 12/2014 | Adair et al. |
| 2015/0041865 A1* | 2/2015 | Storm ................ H04N 5/355 257/229 |
| 2015/0163424 A1* | 6/2015 | Morino ................ H04N 5/361 348/243 |
| 2015/0215560 A1 | 7/2015 | Blanquart et al. |
| 2016/0155765 A1 | 6/2016 | Blanquart |
| 2016/0190197 A1 | 6/2016 | Blanquart |
| 2016/0256041 A1 | 9/2016 | Blanquart et al. |
| 2016/0267845 A1* | 9/2016 | Tsuge ................ G09G 3/3233 |
| 2017/0221945 A1 | 8/2017 | Blanquart |
| 2019/0007588 A1 | 1/2019 | Blanquart et al. |
| 2019/0008375 A1 | 1/2019 | Blanquart et al. |
| 2019/0068909 A1 | 2/2019 | Kaibara |
| 2019/0137609 A1* | 5/2019 | Roy ................ G01S 17/42 |
| 2019/0273881 A1* | 9/2019 | Kawai ................ H04N 5/361 |
| 2020/0003874 A1* | 1/2020 | Moriyama ........... H01L 27/1461 |

FOREIGN PATENT DOCUMENTS

| | | | |
|---|---|---|---|
| CN | 1398407 | A | 2/2003 |
| CN | 1953193 | A | 4/2007 |
| CN | 1992821 | A | 7/2007 |
| CN | 100407433 | C | 7/2008 |
| CN | 101314154 | | 7/2008 |
| CN | 101281918 | A | 10/2008 |
| CN | 100502024 | C | 6/2009 |
| CN | 101640211 | A | 2/2010 |
| CN | 101013714 | B | 5/2010 |
| CN | 101715644 | A | 5/2010 |
| CN | 101848344 | | 9/2010 |
| CN | 101939841 | A | 1/2011 |
| CN | 101978598 | A | 2/2011 |
| CN | 102006427 | A | 4/2011 |
| CN | 102266217 | A | 12/2011 |
| CN | 102397049 | A | 4/2012 |
| CN | 102450998 | A | 5/2012 |
| CN | 103094653 | A | 5/2013 |
| CN | 103636000 | A | 3/2014 |
| CN | 103650476 | A | 3/2014 |
| CN | 2012800337461 | B | 10/2016 |
| EP | 1618833 | A1 | 1/2006 |
| EP | 1628348 | A1 | 2/2006 |
| EP | 2108305 | A1 | 10/2009 |
| EP | 2234387 | A1 | 9/2010 |
| EP | 2302905 | A1 | 3/2011 |
| EP | 2442558 | A1 | 4/2012 |
| EP | 1845835 | B1 | 11/2014 |
| IL | 229396 | | 7/2016 |
| IL | 229397 | | 7/2016 |
| JP | 1993268534 | | 10/1993 |
| JP | H05-268534 | | 5/1995 |
| JP | H09-140664 | | 12/1998 |
| JP | 2001339057 | | 7/2001 |
| JP | 2002329851 | | 11/2002 |
| JP | 2004241490 | | 8/2004 |
| JP | 2004348676 | | 12/2004 |
| JP | 2006025852 | | 2/2006 |
| JP | 2006049361 | | 2/2006 |
| JP | 2007043433 | | 2/2007 |
| JP | 2007214191 | | 8/2007 |
| JP | 2007214772 | | 8/2007 |
| JP | 2007228460 | | 9/2007 |
| JP | 200848313 | | 2/2008 |
| JP | 2008235478 | | 10/2008 |
| JP | 2008290817 | A | 12/2008 |
| JP | Hei 07-136109 | A | 12/2008 |
| JP | 2009005329 | | 1/2009 |
| JP | 2009100380 | | 5/2009 |
| JP | 2009206958 | A | 9/2009 |
| JP | 2010200109 | | 9/2010 |
| JP | 2010252396 | | 11/2010 |
| JP | 2010273757 | | 12/2010 |
| JP | 2011050969 | | 3/2011 |
| JP | 2011114733 | | 6/2011 |
| JP | 2012030004 | | 2/2012 |
| JP | 2014514891 | A | 6/2014 |
| JP | 2014515955 | A | 7/2014 |
| JP | 2016520341 | A | 7/2016 |
| KR | 1020100106920 | | 10/2010 |
| KR | 1020100126749 | | 12/2010 |
| WO | 9413191 | | 6/1994 |
| WO | 1996005693 | A1 | 2/1996 |
| WO | 200108549 | A1 | 2/2001 |
| WO | 2004093438 | | 10/2004 |
| WO | 2006080015 | A2 | 8/2006 |
| WO | 2006129762 | A1 | 12/2006 |
| WO | 2009120228 | A1 | 10/2009 |
| WO | 2009135255 | | 11/2009 |
| WO | 2012155142 | A1 | 11/2012 |
| WO | 2012155143 | A1 | 11/2012 |
| WO | 2012155150 | A1 | 11/2012 |
| WO | 2012155152 | A1 | 11/2012 |
| WO | 2014018948 | A2 | 1/2014 |
| WO | 2014145246 | A1 | 9/2014 |
| WO | 2014145248 | A1 | 9/2014 |

* cited by examiner

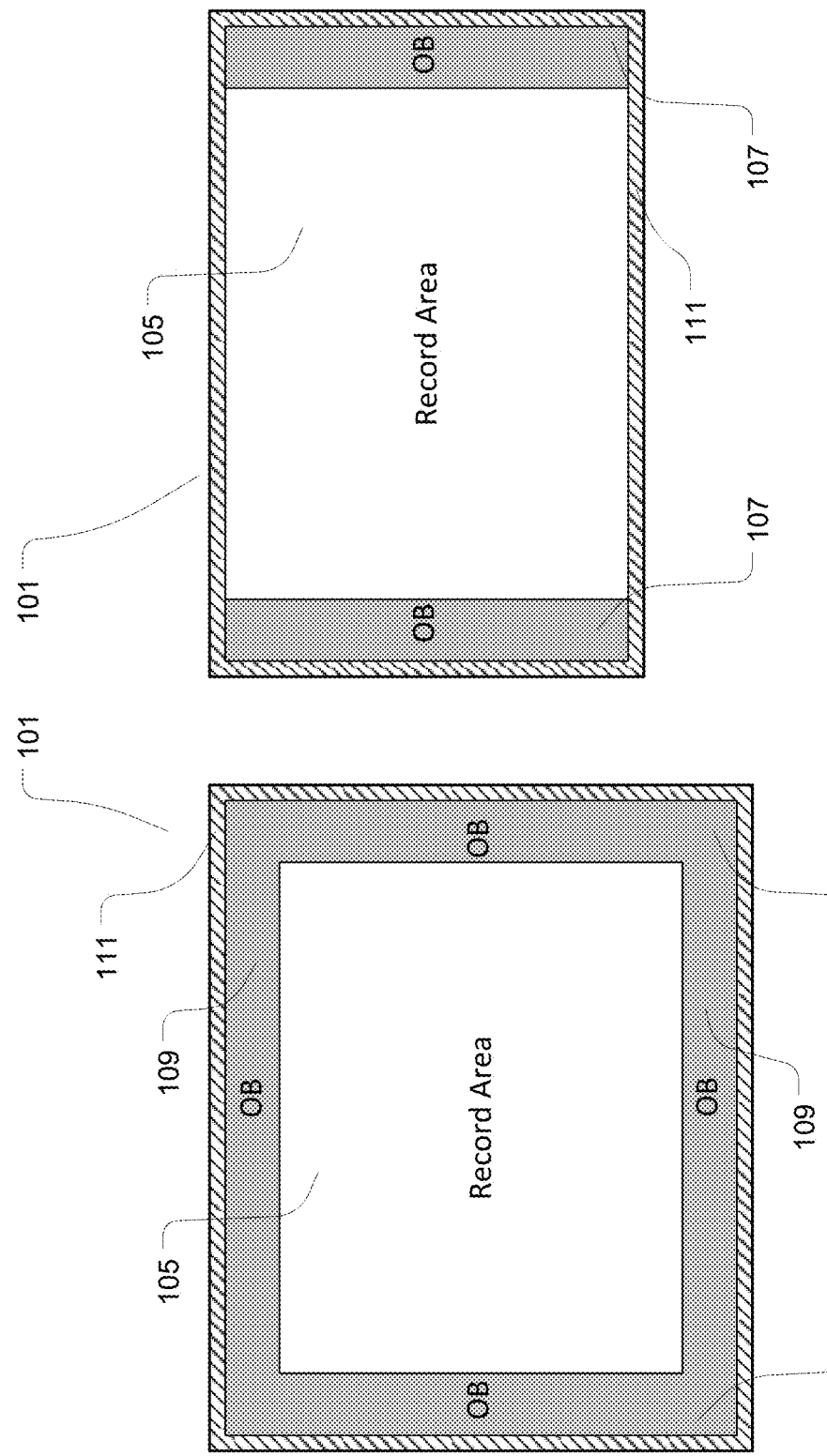

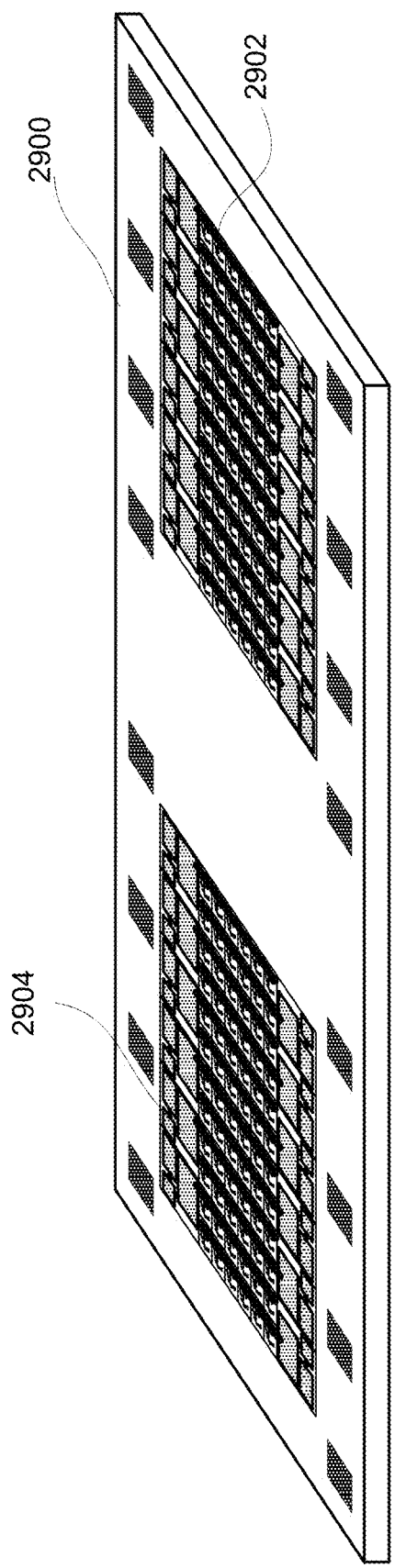
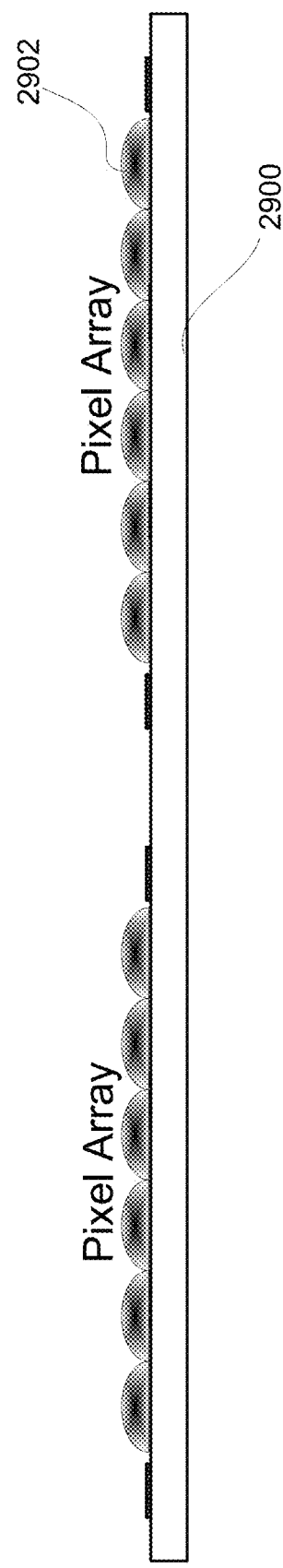
FIG. 11A
FIG. 11B

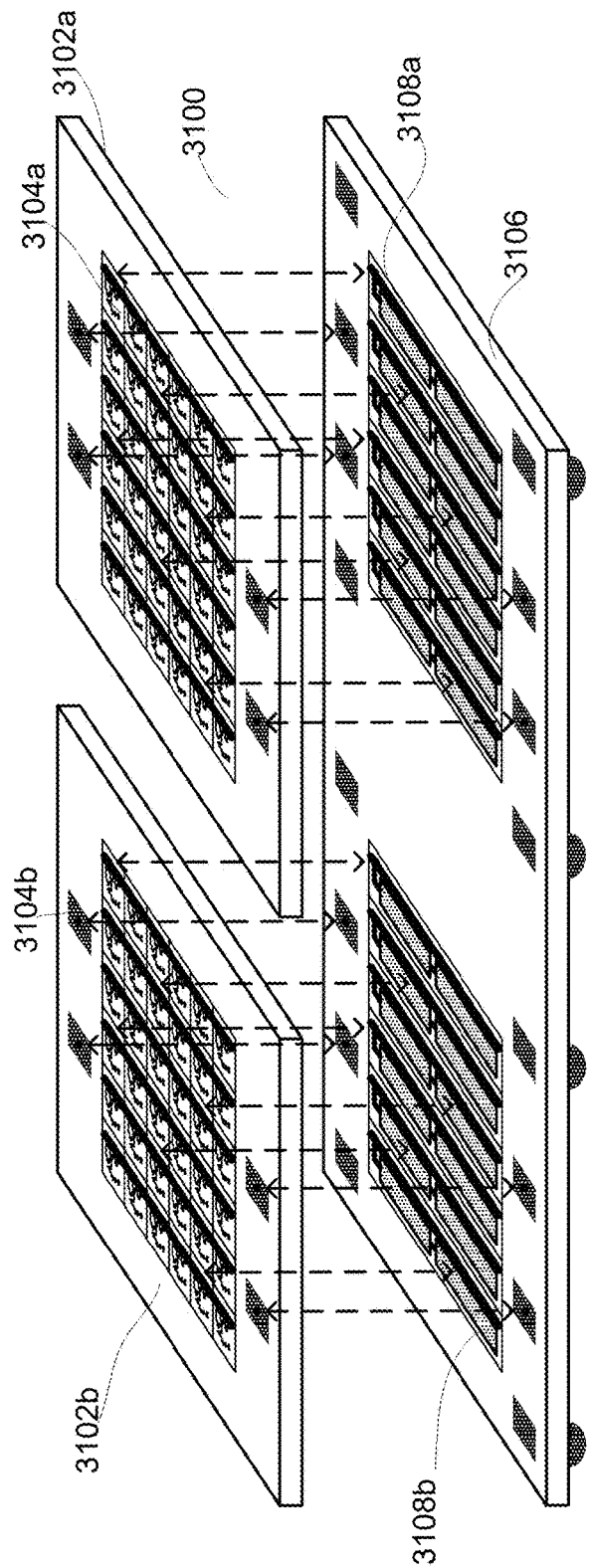
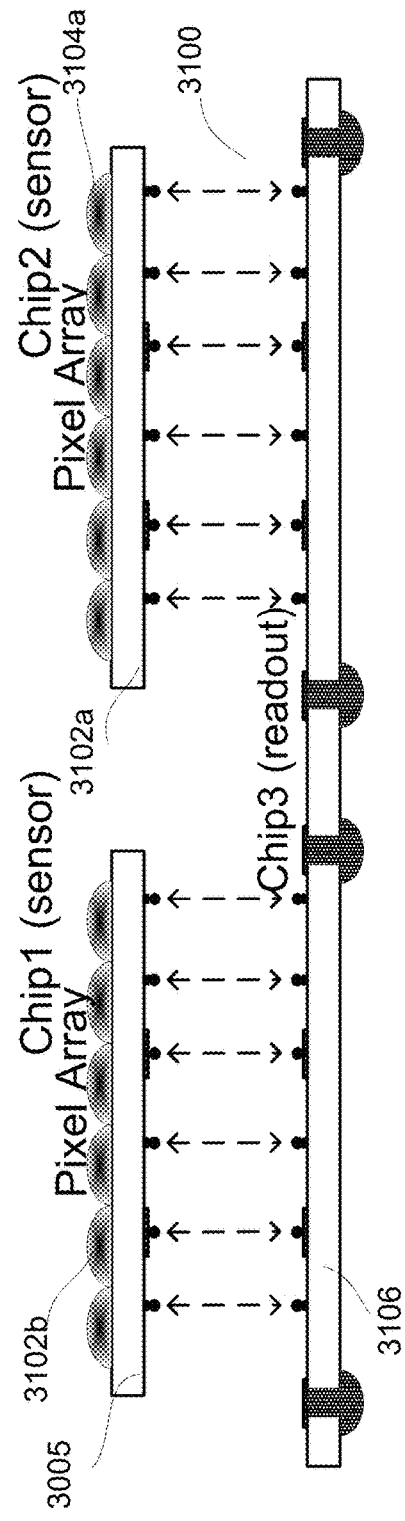
FIG. 13A
FIG. 13B

CAMERA SYSTEM WITH MINIMAL AREA MONOLITHIC CMOS IMAGE SENSOR

CROSS-REFERENCE TO RELATED APPLICATIONS

This application is a continuation of U.S. patent application Ser. No. 15/284,085, filed Oct. 3, 2016 (U.S. Pat. No. 10,075,626), which is a continuation of U.S. patent application Ser. No. 13/952,550, filed on Jul. 26, 2013 (U.S. Pat. No. 9,462,234, issued on Oct. 4, 2016) and claims the benefit of U.S. Provisional Patent Application No. 61/676,289, filed on Jul. 26, 2012, and U.S. Provisional Patent Application No. 61/790,590, filed on Mar. 15, 2013, which are hereby incorporated herein by reference in their entireties, including but not limited to those portions that specifically appear hereinafter, the incorporation by reference being made with the following exception: In the event that any portion of the above-referenced applications is inconsistent with this application, this application supersedes said above-referenced applications.

BACKGROUND

Advances in technology have provided advances in imaging capabilities for medical use. One area that has enjoyed some of the most beneficial advances may be that of endoscopic surgical procedures because of the advances in the components that make up an endoscope. Conventional endoscopes used in, e.g., arthroscopy and laparoscopy are designed such that the image sensors are placed at the proximal end of the device, within the hand-piece unit. In such a configuration, the endoscope unit should transmit the incident light along its length toward the sensor via a complex set of precisely coupled optical components, with minimal loss and distortion. The cost of the endoscope unit may be dominated by the optics, since the components are expensive and the manufacturing process may be labor intensive. Furthermore, this type of scope may be mechanically delicate and relatively minor impacts can easily damage the components or upset the relative alignments thereof. This necessitates frequent, expensive repair cycles in order to maintain image quality.

What may be needed are methods and systems for providing reduced area image sensors for endoscopic medical use that may be capable of maintaining high quality video streams in reduced light environments. Reducing the area of the sensor allows it to be located at the distal end of the endoscope, therefore greatly reducing cost. This introduces the possibility of single-use endoscopes, requiring no repair or sterilization cycles. Alternatively they may be disassembled after and have some of their components recycled.

As may be seen, the disclosure provides methods and systems that can do this in an efficient and elegant manner that will be disclosed herein and will be further enabled by the discussion in the specification and the accompanying figures.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure may become better understood with regard to the following description and accompanying drawings where:

FIG. 1A illustrates an implementation of a pixel array common in the prior art;

FIG. 1B illustrates an implementation of a pixel array made in accordance with the principles and teachings of the disclosure having optical black pixels formed into optical black columns;

FIGS. 11A and 11B illustrate an implementation having a plurality of pixel arrays for producing a three dimensional image in accordance with the teachings and principles of the disclosure;

FIGS. 13A and 13B illustrate a perspective view and a side view, respectively, of an implementation of an imaging sensor having a plurality of pixel arrays for producing a three dimensional image, wherein the plurality of pixel arrays and the image sensor are built on a plurality of substrates.

DETAILED DESCRIPTION

Figure 1C:
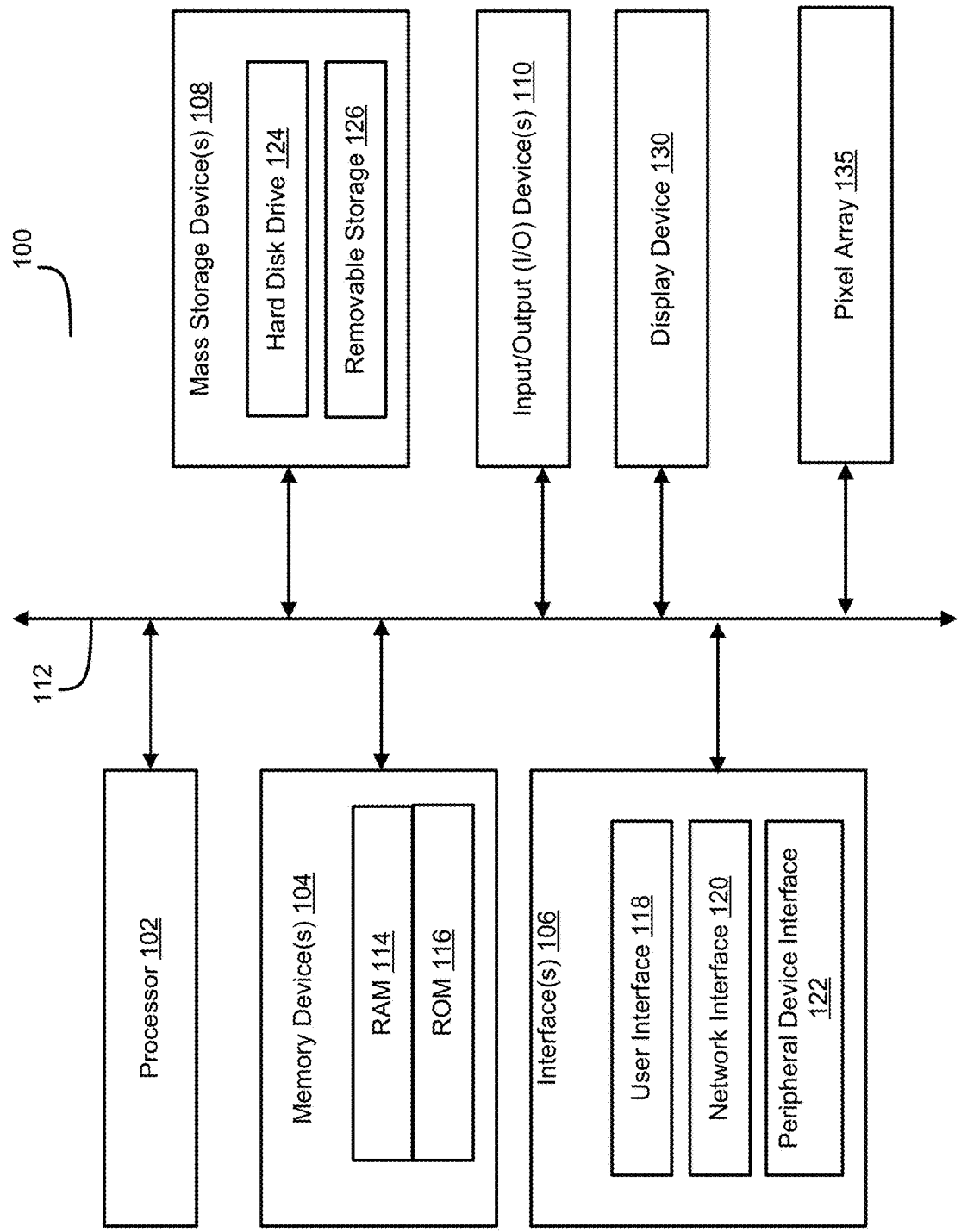
FIG. 1C illustrates a schematic of system circuitry and complementary system hardware in accordance with the principles and teachings of the disclosure.

The disclosure extends to methods, systems, and computer program products for providing advanced endoscopes and uses thereof during medical procedures. In the following discussion of the disclosure, reference may be made to the accompanying drawings, which form a part hereof, and in which may be shown by way of illustration specific implementations in which the disclosure may be practiced. It may be understood that other implementations may be utilized, and structural changes may be made without departing from the scope of the disclosure.

Conventional endoscopes used in arthroscopy and laparoscopy are designed such that the image sensors are placed at the proximal end of the device, within the hand-piece unit. In such a configuration, the endoscope unit should transmit the incident light along its length toward the sensor via a complex set of precisely coupled optical components, with minimal loss and distortion. The cost of the endoscope unit may be dictated by the costs associated with the optics, since the components are expensive and the manufacturing process may be labor intensive.

A solution to the above short comings may be to place the image sensor within the endoscope itself at the distal end within the lumen, thereby potentially providing greater optical simplicity, robustness and economy that may be universally realized within related devices such as for example cell phone cameras. An acceptable solution to this approach may be by no means trivial however as it introduces its own set of engineering challenges, not least of which may be the fact that the sensor should fit within a highly confined area.

Placing aggressive constraints on sensor area may result in fewer and/or smaller pixels. Accordingly, lowering the pixel count directly affects the spatial resolution. Reducing the pixel area also may reduce the available signal capacity and the sensitivity. Lowering the signal capacity reduces the dynamic range i.e. the ability of the camera to simultaneously capture all of the useful information from scenes with large ranges of luminosity. There are various methods to extend the dynamic range of imaging systems beyond that of the pixel itself. All of them have some kind of penalty however, (e.g. in resolution or frame rate) and they can introduce or emphasize undesirable artifacts which become problematic in extreme cases. Alternatively, reducing the sensitivity has the consequence that greater light power may be required to bring the darker regions of the scene to acceptable signal levels. Lowering the F-number may compensate for a loss in sensitivity too, but at the cost of spatial distortion and reduced depth of focus.

In imaging sensor technology, CMOS images sensors have largely displaced conventional CCD imagers in modern camera applications such as endoscopy, owing to their greater ease of integration and operation, superior or comparable image quality, greater versatility and lower cost. Yet CMOS sensors bring certain undesirable traits that should be accounted for in order to achieve optimal results.

Image sensors may include the circuitry necessary to convert the image information into digital data and may have various levels of digital processing incorporated on the sensor chip itself. The digital processes may range from basic algorithms for the purpose of correcting non-idealities of the CMOS sensors which may arise from variations in amplifier behavior, to full image signal processing (ISP) chains, which provide video data in the standard sRGB color space (cameras-on-chip).

The desired degree of sensor complexity for a given camera system may be driven by several factors, one of which may be the available physical space for the image sensor. The most extreme functionally minimal CMOS sensor would have only the basic pixel array plus a degree of serializing and buffering circuits to drive the analog data off chip. All of the timing signals required to operate and read out the pixels may be provided externally. The need to supply the control signals externally, may add many pads which consume significant real estate that would be better used for gathering light. Therefore it doesn't necessarily follow that minimal functionality near the pixel array equates to minimal area usage because of the need of electrical communication connections.

Figure 9:
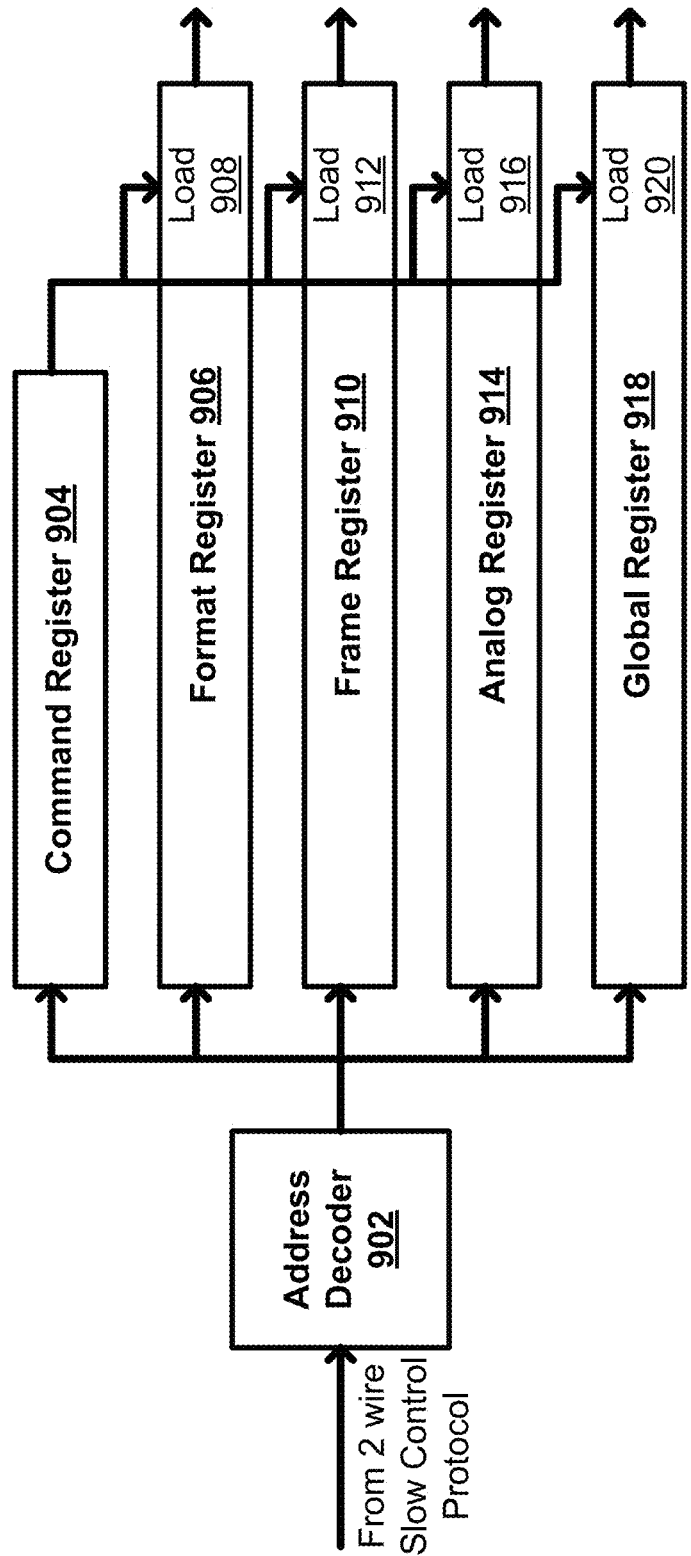
FIG. 9 illustrates a flow chart of an example method according to one implementation.

If the support circuits are to be placed remotely and if the second stage may be an appreciable distance from the sensor, it becomes much more desirable to transmit the data in the digital domain, because it may be rendered nearly immune to interference noise and signal degradation. There may be a strong desire to minimize the number of conductors since that reduces the number of pads on the sensor (which consume space), in addition to increasing the complexity and cost of camera manufacture. Although the addition of analog to digital conversion to the sensor may be necessitated, the additional area may be offset to a degree, of not having to compensate for the signal degradation associated with buffering and transmitting an analog signal. In terms of area consumption, given the typical feature size available in CIS technologies, it may be preferable to have all of the internal logic signals be generated on chip via a set of control registers and a simple command interface controlling the registers as seen in FIG. 9.

High definition imaging with reduced pixel counts in a highly controlled illumination environment may be accomplished by virtue of frame by frame pulsed color switching at the light source in conjunction with high frames capture rates and a specially designed monochromatic sensor. Since the pixels of a reduced area image sensor may be color agnostic, the effective spatial resolution may be appreciably higher than for their color (usually Bayer-pattern filtered) counterparts in conventional single-sensor cameras. They also may have higher quantum efficiency since far fewer incident photons are wasted. Moreover, Bayer based spatial color modulation requires that the MTF of the accompanying optics be lowered compared with the monochrome case, in order to blur out the color artifacts associated with the Bayer pattern. This has a detrimental impact on the actual spatial resolution that can be realized with color sensors.

This particular disclosure may be also concerned with a system solution for endoscopy applications in which the image sensor may be resident at the distal end of the endoscope. In striving for a minimal area sensor based system, there are other design aspects that can be developed, as described herein, beyond the obvious reduction in pixel count. In particular, the area of the digital portion of the chip should be minimized, as should the number of connections to the chip (pads). This disclosure describes novel methods that accomplish those goals for the realization of such a system. This involves the design of a full-custom CMOS image sensor with several novel features.

Implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" may be defined as one or more data links that enable the transport of electronic data between computer systems and/or modules and/or other electronic devices. When information may be transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it may be to be understood that the subject matter defined in the appended claims may be not necessarily limited to the described features or acts described above. Rather, the described features and acts are disclosed as example forms of implementing the claims.

Those skilled in the art may appreciate that the disclosure may be practiced in network computing environments with many types of computer system configurations, including, personal computers, desktop computers, laptop computers, message processors, hand-held devices, hand pieces, camera control units, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) and programmable gate arrays (PGA) can be programmed to carry out one or more of the systems and procedures described herein. Certain terms are used throughout the following description and Claims to refer to particular system components. As one skilled in the art may appreciate, components may be referred to by different names. This document does not intend to distinguish between components that differ in name, but not function.

Image sensors may incorporate special purpose, optically blind or optical black (OB) rows (at the top and/or bottom of the array) and columns (to the right and/or left of the array), for the purpose of offset calibration. An example layout of an image sensor 101 having pixels 105 in a record area along with top and bottom OB rows 109, and left and right OB columns 107 may be shown in FIG. 1A. The OB rows 109 are usually used to monitor the analog pixel black level, for the OB clamp algorithm. OB rows 109 are also typically used by a digital algorithm for the purpose of cancelling column fixed pattern noise or FPN (CFPN). In an embodiment, a guard ring 111 may surround the circumference of the image sensor 101. OB columns 107 on the other hand, usually have the purpose of assessing the line offset as a means to cancel out any line-noise. Since line-noise may be temporal, the offset should be computed anew for each line in every frame.

An overall reduction in the size of the pixel array can be achieved by removing the OB rows 109 and using the OB columns 107 instead of OB rows 109 for the OB clamp algorithm (see discussion below). In an implementation, all FPN types, including CFPN, may be cancelled by acquiring frames of dark data, thereby negating the need for a dedicated CFPN correction and its associated OB rows 109. FIG. 1B shows an example of just such an image sensor 101 and a pixel array 105 in which there are no OB rows present, but instead comprise OB columns 107.

FIG. 1C may be a block diagram illustrating an example computing device 100. Computing device 100 may be used to perform various procedures, such as those discussed herein. Computing device 100 can function as a server, a client, or any other computing entity. Computing device can perform various monitoring functions as discussed herein, and can execute one or more application programs, such as the application programs described herein. Computing device 100 can be any of a wide variety of computing devices, such as a desktop computer, a notebook computer, a server computer, a handheld computer, tablet computer and the like.

Computing device 100 includes one or more processor(s) 102, one or more memory device(s) 104, one or more interface(s) 106, one or more mass storage device(s) 108, one or more Input/Output (I/O) device(s) 110, and a display device 130 all of which are coupled to a bus 112. Processor(s) 102 include one or more processors or controllers that execute instructions stored in memory device(s) 104 and/or mass storage device(s) 108. Processor(s) 102 may also include various types of computer-readable media, such as cache memory.

Memory device(s) 104 include various computer-readable media, such as volatile memory (e.g., random access memory (RAM) 114) and/or nonvolatile memory (e.g., read-only memory (ROM) 116). Memory device(s) 104 may also include rewritable ROM, such as Flash memory.

Mass storage device(s) 108 include various computer readable media, such as magnetic tapes, magnetic disks, optical disks, solid-state memory (e.g., Flash memory), and so forth. As shown in FIG. 1C, a particular mass storage device may be a hard disk drive 124. Various drives may also be included in mass storage device(s) 108 to enable reading from and/or writing to the various computer readable media. Mass storage device(s) 108 include removable media 126 and/or non-removable media.

I/O device(s) 110 include various devices that allow data and/or other information to be input to or retrieved from computing device 100. Example I/O device(s) 110 include cursor control devices, keyboards, keypads, microphones, monitors or other display devices, speakers, printers, network interface cards, modems, lenses, CCDs or other image capture devices, and the like.

Display device 130 includes any type of device capable of displaying information to one or more users of computing device 100. Examples of display device 130 include a monitor, display terminal, video projection device, and the like.

A pixel array 135 may also be included and may operate remotely relative to other circuits within the system.

Interface(s) 106 include various interfaces that allow computing device 100 to interact with other systems, devices, or computing environments. Example interface(s) 106 may include any number of different network interfaces 120, such as interfaces to local area networks (LANs), wide area networks (WANs), wireless networks, and the Internet. Other interface(s) include user interface 118 and peripheral device interface 122. The interface(s) 106 may also include one or more user interface elements 118. The interface(s) 106 may also include one or more peripheral interfaces such as interfaces for printers, pointing devices (mice, track pad, etc.), keyboards, and the like.

Bus 112 allows processor(s) 102, memory device(s) 104, interface(s) 106, mass storage device(s) 108, and I/O device(s) 110 to communicate with one another, as well as other devices or components coupled to bus 112. Bus 112 represents one or more of several types of bus structures, such as a system bus, PCI bus, IEEE 1394 bus, USB bus, and so forth.

For purposes of illustration, programs and other executable program components are shown herein as discrete blocks, although it may be understood that such programs and components may reside at various times in different storage components of computing device 100, and are executed by processor(s) 102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein on the fly or before the initialization of the system.

Figure 2:
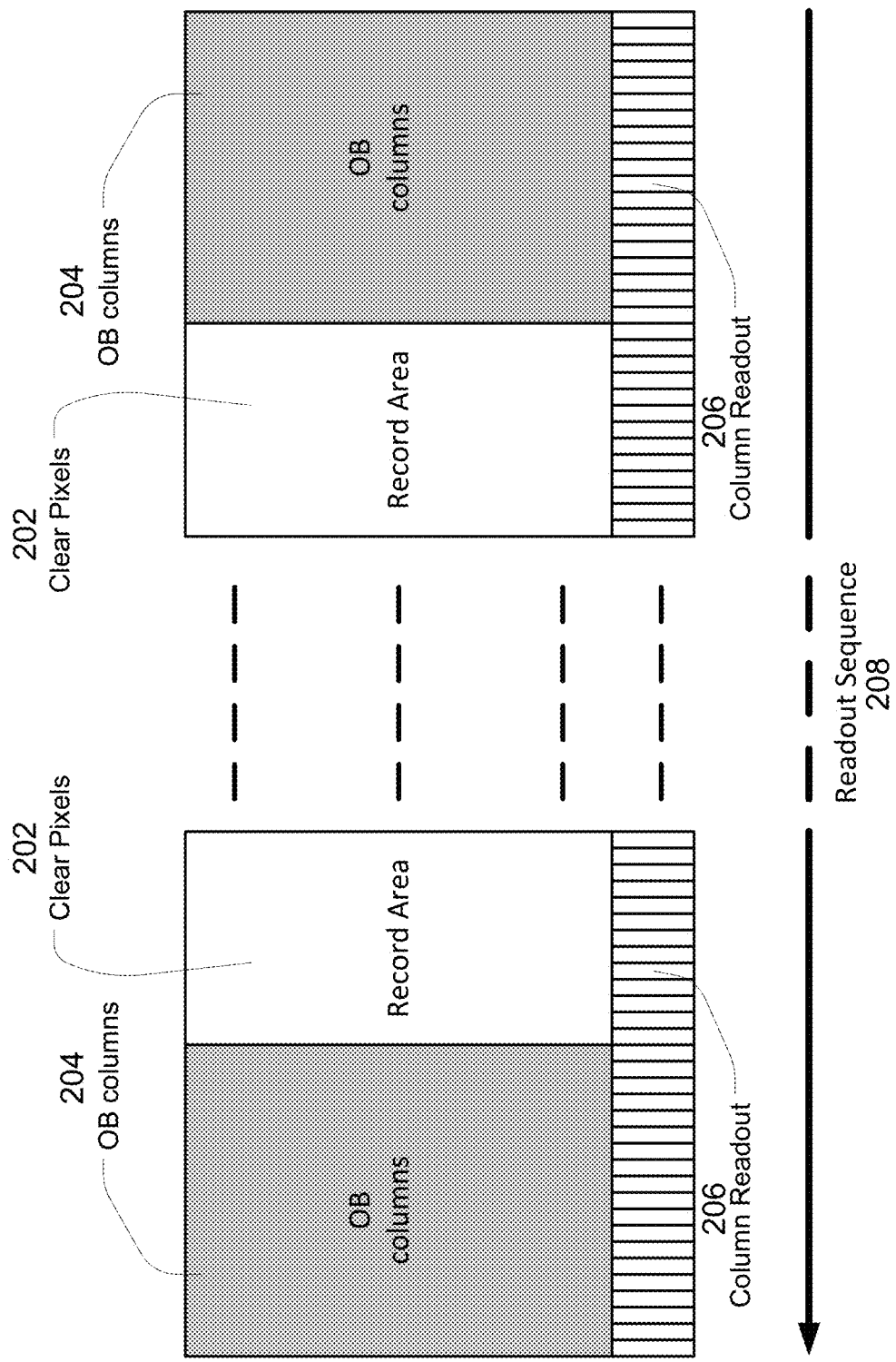
FIG. 2 illustrates an example pixel array showing the relationships between active recording pixel columns and optical black pixel columns in accordance with the principles and teachings of the disclosure.
Figure 3:
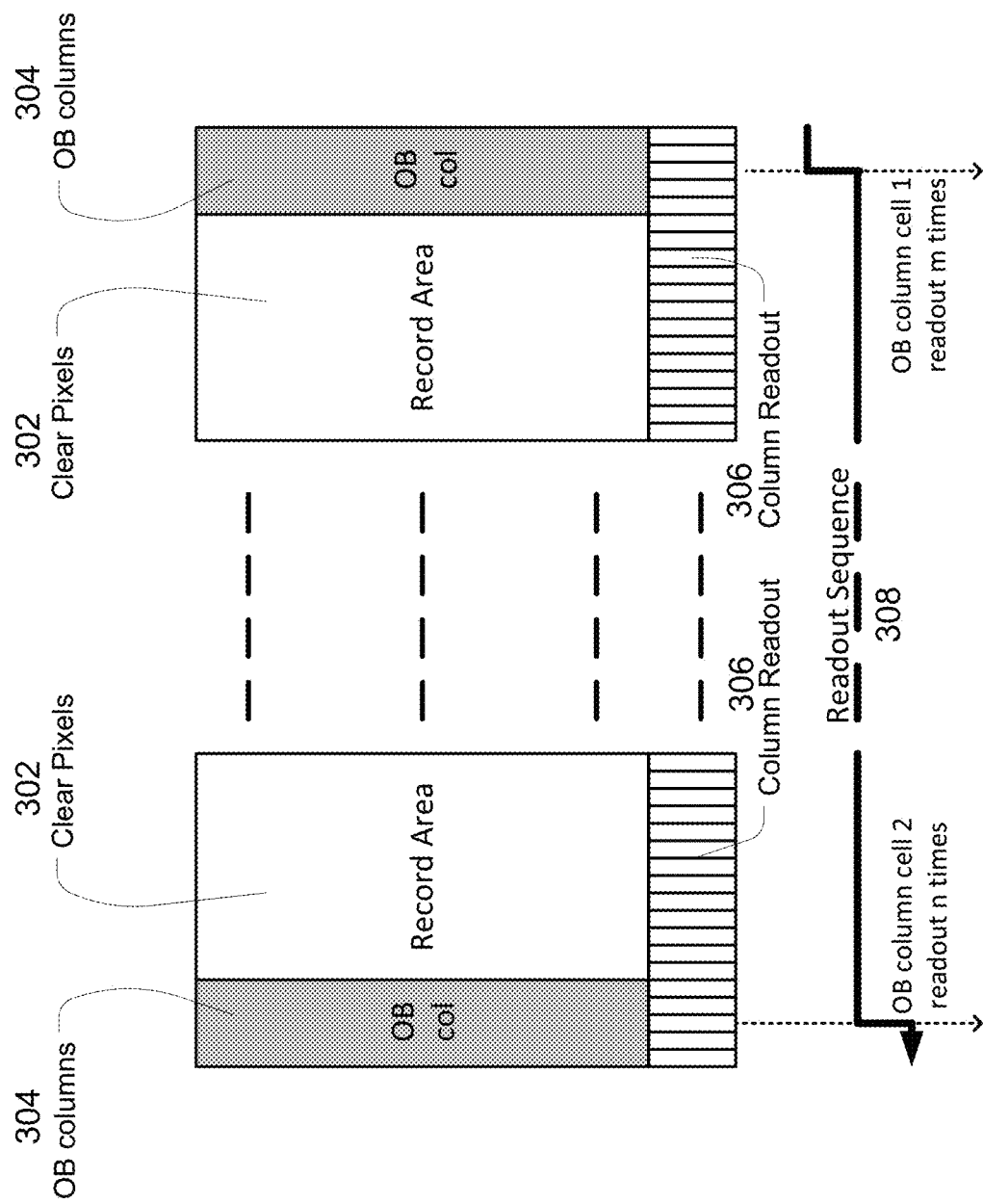
FIG. 3 illustrates an example pixel array showing the relationships between active recording pixel columns and reduced number of optical black pixel columns in accordance with the principles and teachings of the disclosure.

The number of OB columns might typically be 100 or more, depending on space constraints etc. The more OBs that are available the greater the line-offset precision may be. Greater precision means lower line noise, post-correction. Normally, all of the available physical OBs would be read for each line as shown in FIG. 2. A further degree of array size reduction can be achieved if, instead of having the requisite number of physical OB pixels, (given a certain precision target), a smaller number of physical pixels are implemented are they re-sampled multiple times during the horizontal readout process. This approach is illustrated in FIG. 3.

Raw CMOS image sensor data present at the output of the digitizer may be far from ideal. It may often be the case that the optimal order with which to read out a horizontal row of pixels does not equate to the actual physical order within the array. Also, raw data usually reveals undesirable artifacts that reflect the nature of the readout architecture too, which become very evident in situations of low light and correspondingly high gain. These readout artifacts may typically include column FPN, arising from the variation in offset from column to column and temporal line-noise which can result from circuit resets associated with the horizontal readout process.

Figure 4:
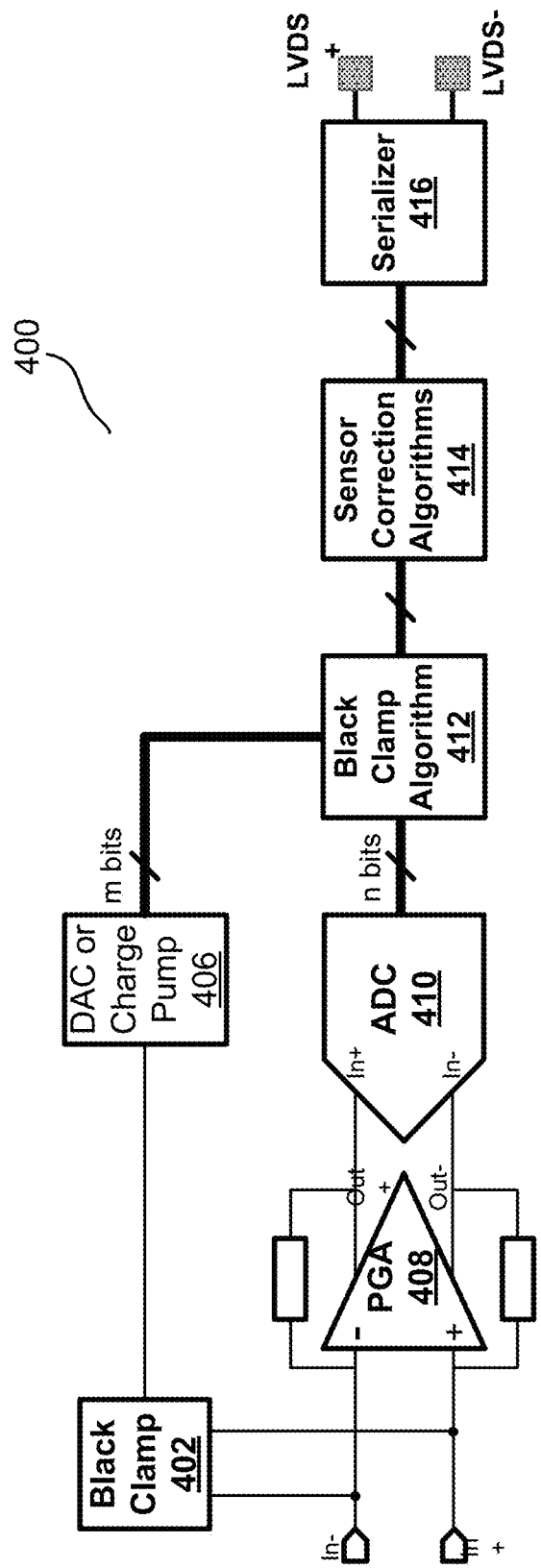
FIG. 4 illustrates a hardware flow chart of an example method according to one implementation in accordance with the principles and teachings of the disclosure.

Another property of CMOS sensors may be that a certain degree of dark signal may be generated by the photodiode within the pixel. The amount of integrated signal arising from this current depends on both the exposure time and the temperature. Since this dark signal may be indistinguishable from photo-signal, changes in it translate to changes in signal pedestal in the analog domain. In order that the available dynamic range of the ADC be fully exploited, it may be important that the dark signal be sampled and adjusted for. FIG. 4 illustrates how this may be usually done in CMOS sensors. Data from the OB pixels may be averaged in the on-chip logic and compared to a target digital black level. Continuous adjustments are made to an input offset voltage in order to make the black level as close to the target as possible. This may be referred to as the black clamp or OB clamp process.

The majority of commercially available sensors incorporate the logic on-chip to perform the black-clamp and the digital noise corrections. This logic does not have to be resident on sensor, however and in an effort to develop a camera system with a minimal area sensor, it makes sense to migrate these corrections to the image signal processing chain (ISP). This actually has a net advantage as regards overall system performance, since the corrections are less resource limited if they are resident in an FPGA or ASIC with lots of available logic gates and RAM.

Figure 5:
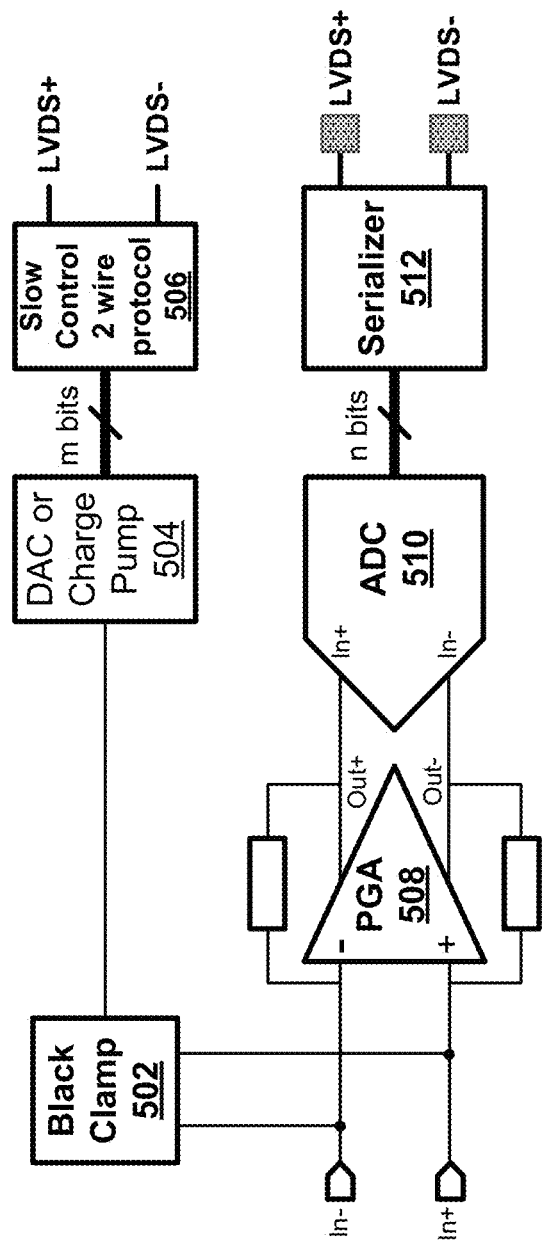
FIG. 5 illustrates a hardware flow chart of an example method according to one implementation in accordance with the principles and teachings of the disclosure.

FIG. 5 shows how the OB clamp logic may be moved off of the sensor (along with the sensor correction algorithms). In this case, information about the analog adjustments from the OB clamp logic may be transmitted to the sensor by means of instructions, via its command interface.

Figure 6:
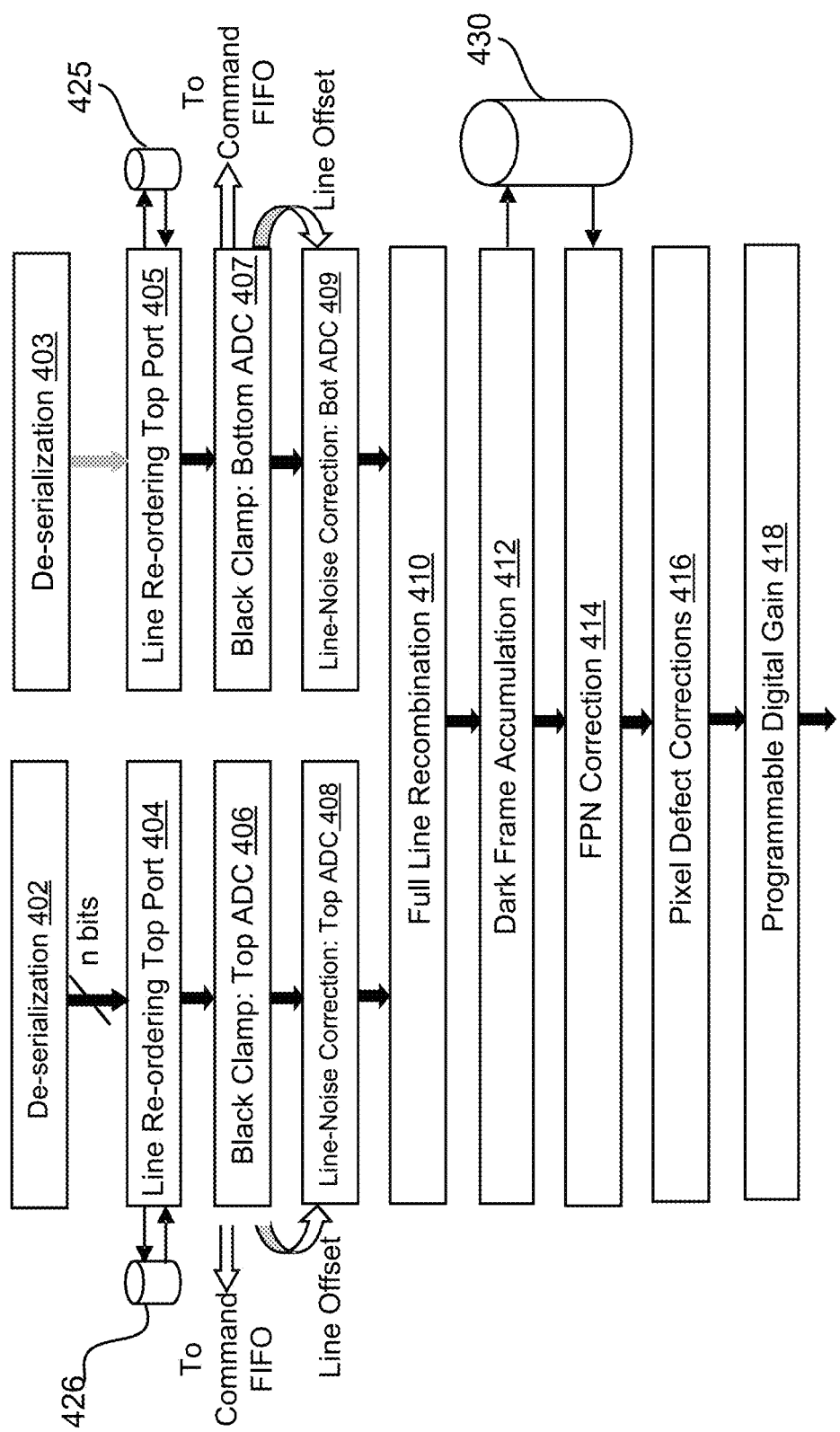
FIG. 6 illustrates a flow chart of an example method and hardware schematics for use with a partitioned light system according to one implementation in accordance with the principles and teachings of the disclosure.

FIG. 6 shows an example implementation of the front-end of an ISP which has been developed in the context of a system incorporating a minimal area sensor. In this example there are two digitizers on the sensor, converting the even and odd-numbered columns respectively and transmitting serial data on two differential ports.

Following de-serialization, the first process may be concerned with reconstructing the line for each port into the appropriate order. The next two correction blocks, dealing with the black clamp and the line noise correction, are both data-path specific, i.e. the two chains would be treated separately.

Figure 7:
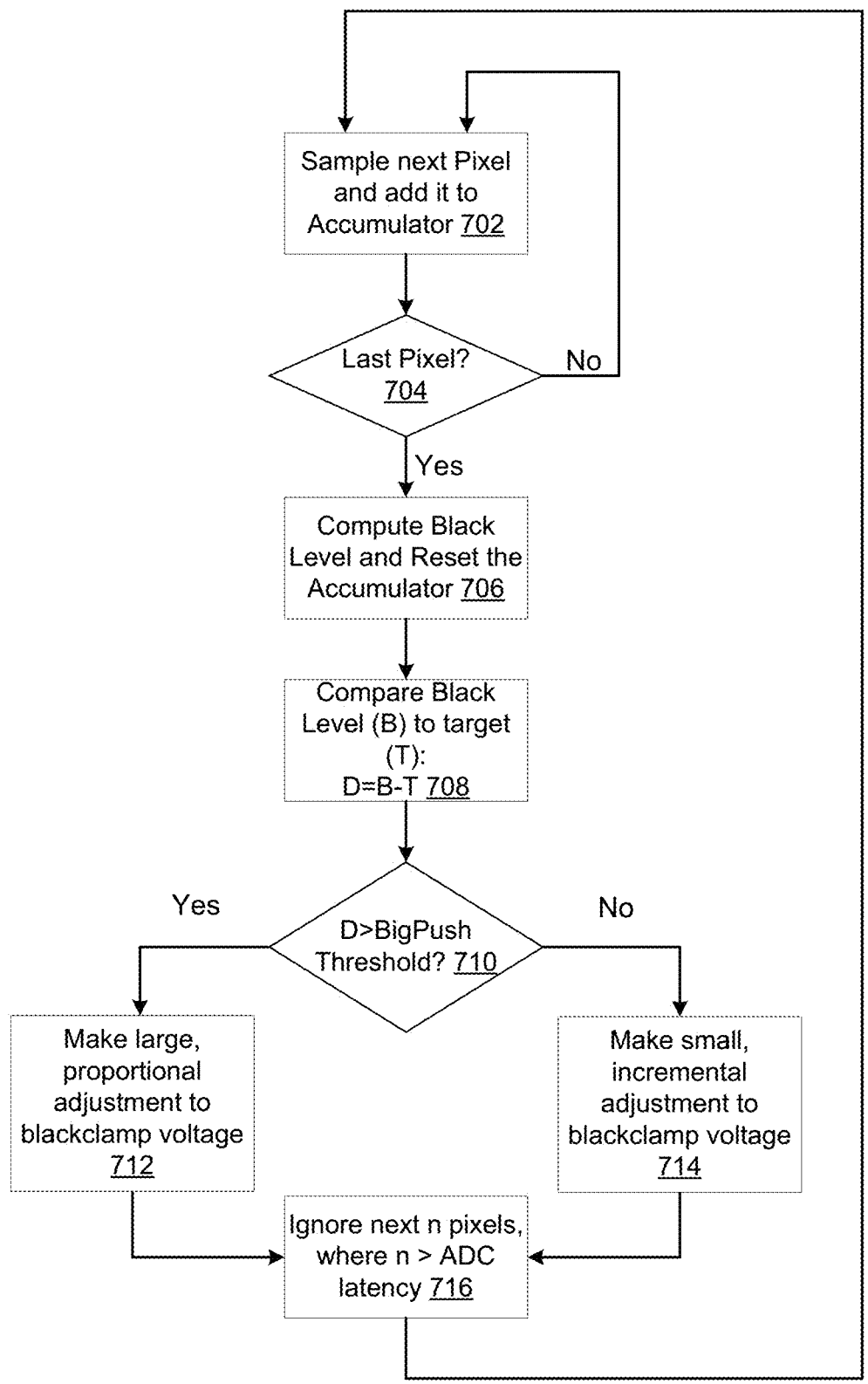
FIG. 7 illustrates a flow chart of an example method according to one implementation in accordance with the principles and teachings of the disclosure.
Figure 8A:
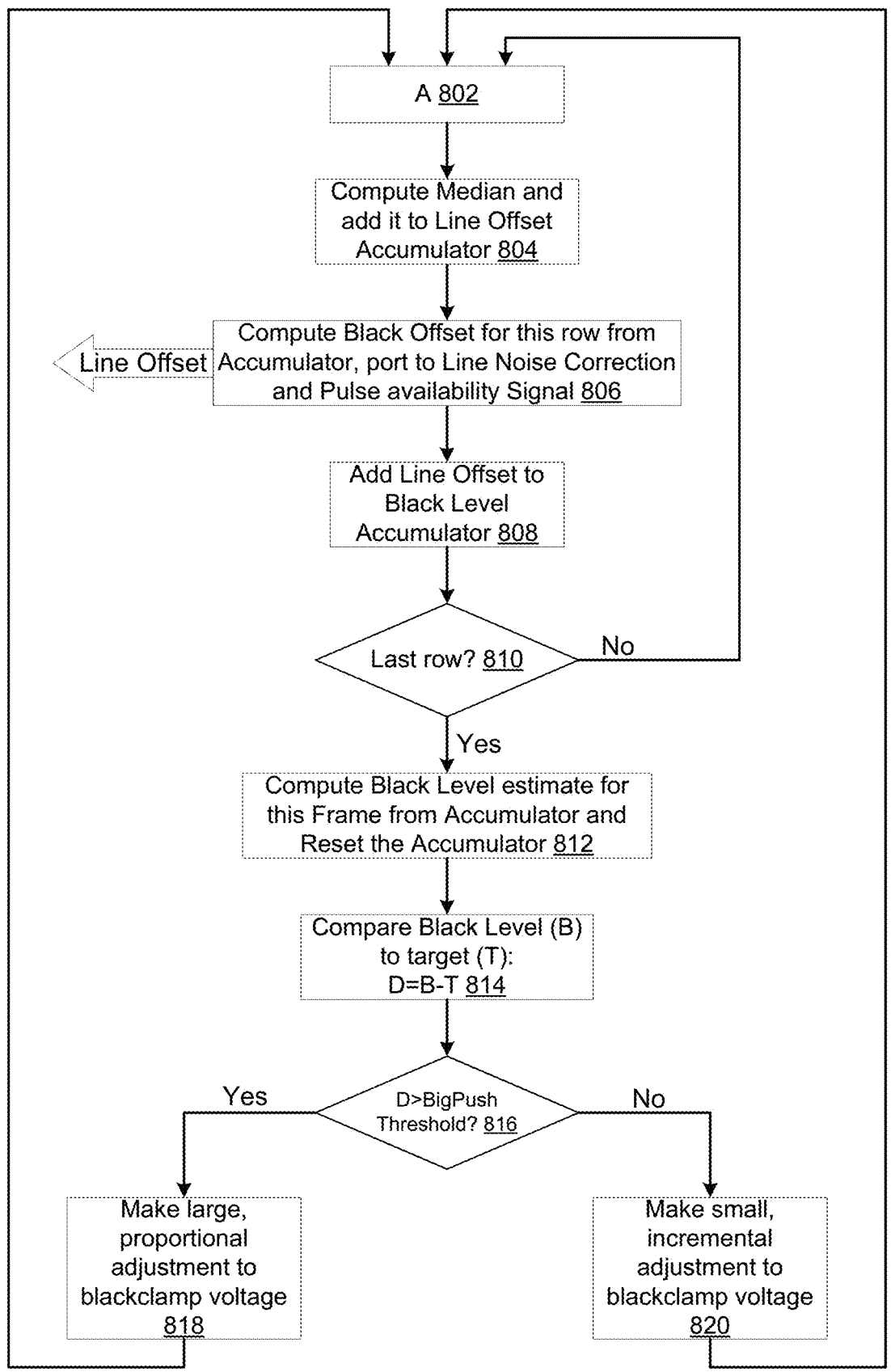
FIG. 8A illustrates a flow chart of an example method according to one implementation in accordance with the principles and teachings of the disclosure.
Figure 8B:
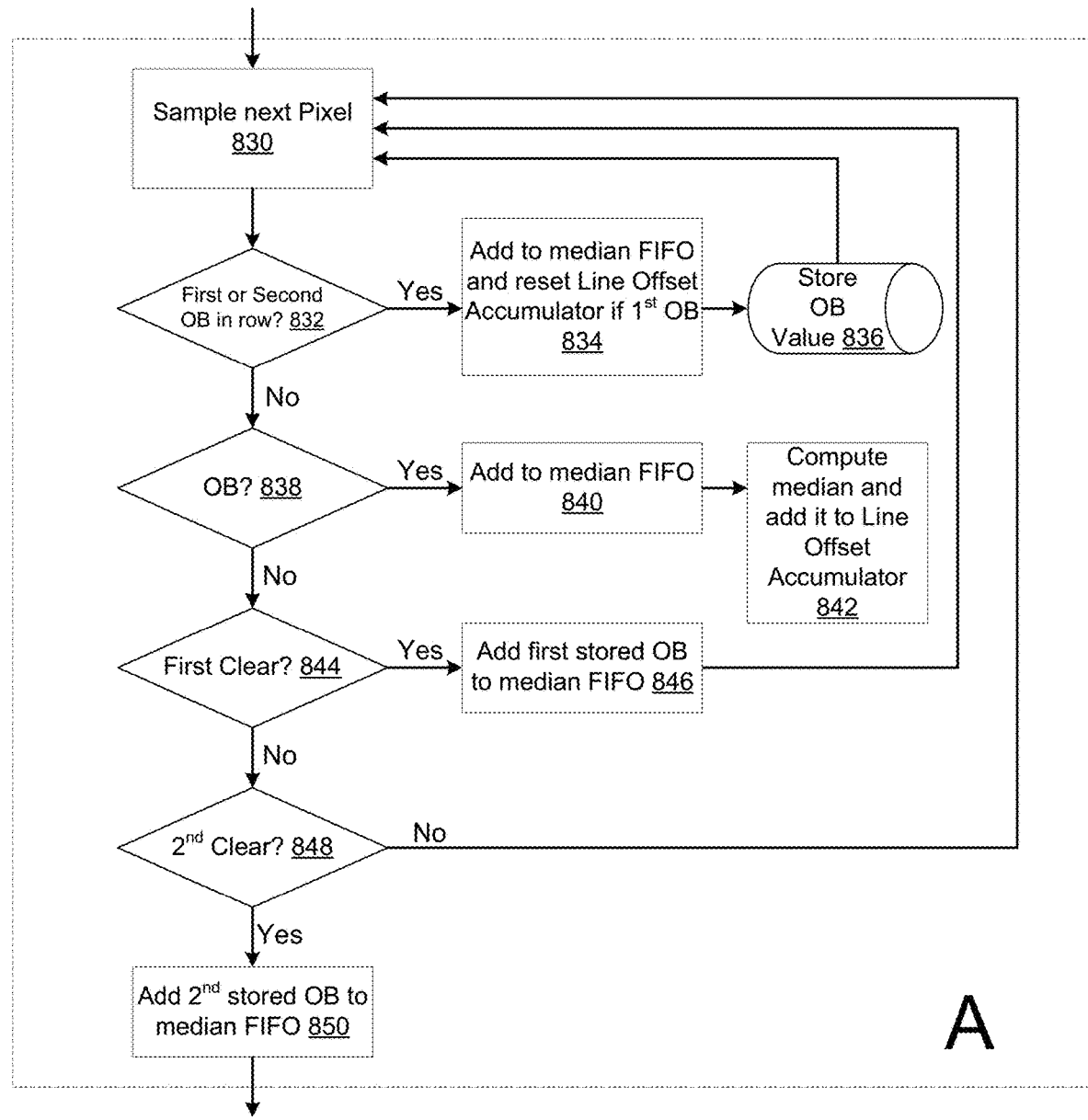
FIG. 8B illustrates a flow chart of an example method according to one implementation in accordance with the principles and teachings of the disclosure.

Black Clamp—The flowchart in FIG. 7 may be an example of how the OB clamp logic might typically operate within a conventional CMOS imaging system on chip. There might typically be multiple samples and analog adjustments made per frame, from multiple OB rows, while the OB-row pixels are present in the digital readout path. As discussed earlier, for a minimal area sensor, the number of OB pixels should be reduced to the minimum necessary and this can be accomplished by eliminating the OB rows and using the OB columns to calibrate the black clamp as well as the line-noise. The flowchart in FIGS. 8A and 8B outline a method of accomplishing this. The basic idea may be to accumulate the set of measured, uncorrected line offsets for the whole frame and use the final estimate to make the black clamp adjustment. Meanwhile each individual line offset estimate may be fed to a later process in order to make a digital adjustment to the individual line.

The adjustment of the black clamp level may be done by means of controlling a DC voltage ($V_{blackclamp}$) using a DAC or charge pump on the sensor. Pixel voltage offsets entering the ADC move around due to dark current in the photodiode e.g., therefore the DAC needs to be regularly adjusted by assessing the black offset in the digital domain.

Individual OB pixels which do not behave normally may badly degrade the quality of the black offset measurements; therefore it may be very important to deal with them. A good approach may be to take for each OB pixel, the median of a group of 5 including the pixel in question and its four nearest neighbors. The final line offset estimate would then be taken as the mean of all the medians. Some provision should be made not to lose statistics at the beginning and the end, such as buffering the whole sample of OBs and wrapping around the sample of 5. This necessitates pipelining the data, resulting in a delay equal to at least the total number of OBs per ADC channel, per row.

Line offset estimate for even channel (assuming two ADCs with odd-even interspersion), row # r:

$$L_{r,even} = \frac{2 \cdot \sum_{i=0,2,4...}^{N_{OB}-2} \mu_i}{N_{OB}}$$

Line offset Where $N_{OB}$ may be the total number of OB pixels per row and $\mu_i$ may be the median for OB pixel i, computed thus:

$$\mu_0 = \text{median}[x_{(N_{OB}-4)}, x_{(N_{OB}-2)}, x_0, x_2, x_4]$$

$$\mu_2 = \text{median}[x_{(N_{OB}-2)}, x_0, x_2, x_4, x_6]$$

$$\mu_4 = \text{median}[x_0, x_2, x_4, x_6, x_8]$$

...

$$\mu_{(N_{OB}-2)} = \text{median}[x_{(N_{OB}-6)}, x_{(N_{OB}-4)}, x_{(N_{OB}-2)}, x_0, x_2]$$

Likewise, line offset estimate for odd channel (assuming two ADCs with odd-even interspersion), row # r:

$$L_{r,odd} = \frac{2 \cdot \sum_{i=1,3,5...}^{N_{OB}-1} \mu_i}{N_{OB}}$$

where $$\mu_1 = \text{median}[x_{(N_{OB}-3)}, x_{(N_{OB}-1)}, x_1, x_3, x_5]$$

$$\mu_3 = \text{median}[x_{(N_{OB}-1)}, x_1, x_3, x_5, x_7]$$

$$\mu_5 = \text{median}[x_1, x_3, x_5, x_7, x_9]$$

...

$$\mu_{(N_{OB}-1)} = \text{median}[x_{(N_{OB}-5)}, x_{(N_{OB}-3)}, x_{(N_{OB}-1)}, x_1, x_3]$$

To get the overall frame black level, a good practical approach may be afforded by accumulating all of the line offsets to compute the overall black level using simple exponential smoothing (SES). The benefit of using SES may be that the rows towards the end of the frame may have a greater influence on the final black estimate which may be desirable for addressing changes in black offset occurring on sub-frame timescales.

In SES, a running estimate may be incrementally adjusted each time a sample may be made available. For convenience the sample can be divided by a binary number ($2^q$) before being added to the previous estimate. The previous estimate may be first multiplied by ($2^q-1$)/$2^q$ each time, in order to normalize the result. High values of q result in greater statistical precision over time in a stable scenario. Lower values of q may make the correction more reactive to rapid changes. q should be made available as a tunable parameter.

$$k_r = L_r \quad (r = 0)$$

$$k_r = \frac{1}{2^q} L_r + \frac{(2^q - 1)}{2^q} k_{(r-1)} \quad (r > 0)$$

where $k_r$ may be the black level estimate after row r and $L_r$ may be the line offset estimate for row r. The decision about what to do with the black clamp DACs may be made after the final row in the array has been added.

The black clamp algorithm would require a target black level which could be provided by an adjustable parameter. The black clamp DAC on the sensor for the channel in question would be pushed up or down, depending on whether the observed black estimate may be above or below the target. The size of the push could be e.g. the smallest unit, i.e. one DAC count, provided the black offset may be close to the target. In the case that the black level may be a long way from the target, a larger proportional push could be made, see FIG. 8A. The algorithm would need to know a rough calibration of the correspondence between black clamp DAC counts and sensor ADC counts and the directionality of DAC adjustments with respect to the output black level.

Line-Noise Correction—'Line-Noise' refers to stochastic, temporal variations in the offset of a horizontal row of pixels. There may be multiple sources, but it can be considered as reset-noise arising from analog elements being reset each time a row of pixels may be read out. It may be temporal and a new correction should be computed for each new line per every frame. Since the amplification stage at the ADC input may be the final analog element, there may be good reason to suspect that the line-noise may appear phenomenologically independent per ADC channel. Therefore the optimal approach may be to correct each ADC (channel) separately.

To eliminate line-noise completely may be impossible, since the sample of OB pixels used for the line offset estimate, may be separate from the sample to which the correction may be being applied (and the sample statistics are finite). Assuming all the noise may be Gaussian, the post-correction line-noise may be approximately equal to the uncertainty in the line offset estimate arising from the pixel temporal noise present in the OB pixels:

$$\sigma_{L,post} \approx \frac{\sigma_P}{\sqrt{N_{OB}}}$$

where $\sigma_{L,post}$ may be the post correction temporal line-noise, $\sigma_{P\ may\ be}$ the OB pixel temporal noise and $N_{OB\ may\ be}$ the number of OB pixels. The line-noise correction also introduces a spatial line-noise component, mostly as a consequence of the pixel FPN present within the OB pixels:

$$FPN_{L,post} \approx \frac{FPN_P}{\sqrt{N_{OB}}}$$

This artifact would be eliminated by the FPN correction, later in the chain. Simulations have indicated that in order for temporal line-noise to be invisible, the magnitude should be less than approximately 1/10 of the pixel temporal noise. This criterion indicates at least 100 OB pixels would be required per line.

Line-noise correction application to optically sighted (clear) pixels:

$$x'_i = x_i - L + B$$

Where L may be the line offset estimate for the current line, ported from the 'Black Clamp' module and B may be the black clamp target level.

Full Line Recombination—This would involve simply combining the two data channels into a full line. They need to be interleaved in such a way that the final clear pixel order reflects the correct order in the array.

FPN Correction—CMOS image sensors have multiple noise sources, the magnitude and appearance of which depend on a range of physical conditions. Pure Poisson or Gaussian temporal noise with no coherent components (e.g. photon shot noise or source follower 1/f read noise) looks as natural as noise can look. All other perceivable noise types may degrade the image quality to a much greater extent for the same amplitude. Spatial noise (FPN) may be especially egregious and CMOS sensors inherently have at least two sources; pixel FPN and column FPN. The pixel FPN may be mostly due to variations in photodiode leakage current (dark signal) from pixel to pixel (DSNU). This source may be exponentially dependent on junction temperature ($T_J$) and linearly dependent on exposure time. Column FPN may be a consequence of the readout architecture, in which pixels from within the same column are channeled through common analog readout elements.

Typically an on-chip digital FPN correction would involve dealing only with the column FPN component, requiring one offset correction register per column. The precision of such a correction might typically be 20 bits or so per column, which translates to around 5 kB of RAM for a 1920×1080 array. One of the benefits of migrating the digital sensor corrections to the ISP may be the ready availability of RAM. This opens up the possibility of a comprehensive FPN correction which cancels out any row, column or pixel-wise component. This may be accomplished by means of simple exponential smoothing (SES) in which each fresh dark frame sample may be used to adjust a running offset estimate on a per physical pixel basis.

Programmable Digital Gain—The final block in FIG. 6 corresponds to a programmable digital amplifier. CMOS iSoCs are usually equipped with digital programmable gain stages with very fine increments. This may be to facilitate auto-exposure processes which typically modulate the gain and the exposure time.

The digital amplifier can be used to align the range of the sensor ADC to the range of the ISP (e.g. ×2 for 11 bit ADC to 12-bit ISP). A small amount of digital gain may also be used to trim off the imprint of the digital line-noise and FPN corrections which becomes apparent at the full range of the ADC.

Minimization of configuration register address ROM—Conventional CMOS image sensors incorporate many writeable registers for the purpose of controlling how the sensor operates. They would typically incorporate DAC settings to adjust bias voltages and currents, timing parameters for, e.g., the pixel acquisition and readout cycle, amplifier offsets and gains etc. The usual convention may be to assign a particular 8-bit or 16-bit address to each register which contains typically 8 or 16 bits of data.

A more space conservative approach involves combining large amounts of control RAM into single, long registers. In the extreme case, all parameters could be placed into a single register, requiring no address ROM. This solution may be not very practical however since writing control registers takes time and typical video applications involve changing a small number of operational parameters (such as exposure time) on a frame-by-frame basis. The most practical solution may be afforded by concatenating functionally related sets of parameters into a small number of long registers. The difference in space implied by having say, ten registers (requiring 4 address bits) versus one, may be negligible. In particular it makes sense that all of the parameters which are written periodically at a high rate (e.g. every frame) belong together in an exclusive register (the frame register), in order to keep the time required to write it to a minimum. Such parameters include the exposure times, gains, incremental offset adjustments and any others necessary to maintain continuous high quality video. If the digital data-path logic has been migrated off chip as described earlier, the black clamp voltage adjustment data also belongs in such a register since it should be revised every frame too. In an implementation, during this configuration phase can registers be written and therefore the timing of the frame register writes with respect to the overall frame timing should be carefully controlled by the camera.

Other examples of parametric register groupings could include; analog currents, analog voltages, pixel timing, vertical timing, sensor commands (resets etc.) and so on.

In FIG. 9 the arrangement of registers may be shown for a specific minimal-area sensor design. The "Command" register may be used for top level event-oriented 1-bit commands such as chip resets and the loads for the other registers shown below it. A 2-wire protocol address decoder decides which shift register to direct incoming 2-wire protocol data toward. To load the "Format" register, e.g., the external controller sends a command with the address associated with the Format register. This places the stream of data into the Format-register shift register. Then in order to latch the data, a follow up command may be sent to the Command register with the particular "load Format" bit set. It will be appreciated that a plurality of control registers may be used. The control registers may be digital latches that may be loaded via shift registers. The shift registers may be arbitrary in length. In an embodiment, a majority of the plurality of control registers may be loaded using shift registers that include many tens of bits. In an embodiment, a majority of the plurality of control registers may be loaded using shift registers that include hundreds of bits. In an embodiment, a majority of the plurality of control registers may be loaded using shift registers that include thousands of bits. In an embodiment, the shift registers may be loaded using a serial, 2-wire protocol. In an embodiment, one of the shift registers may be dedicated to frame-to-frame parameter changes, such as, e.g., integration times and black clamp offset adjustments.

Figure 10:
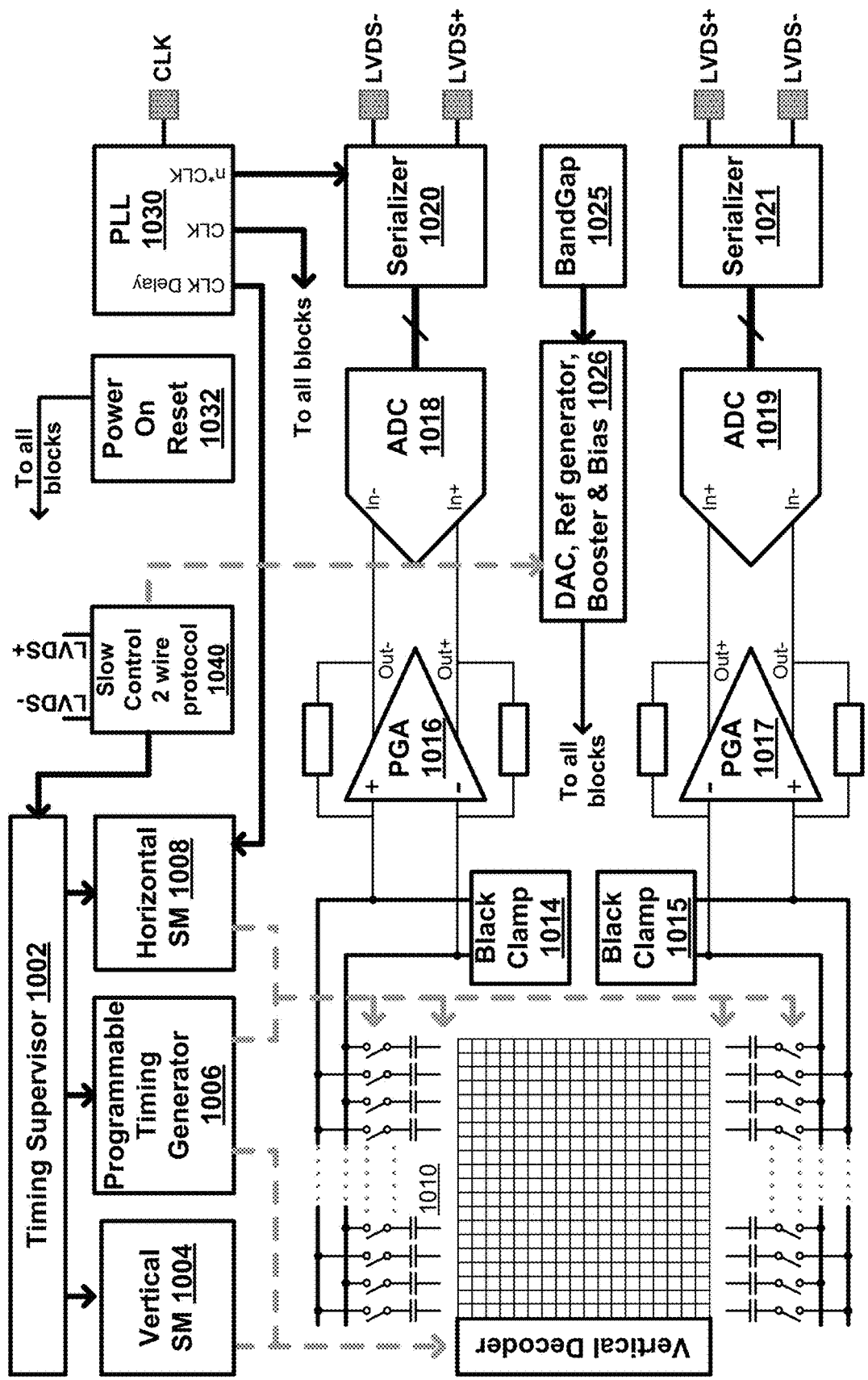
FIG. 10 illustrates a hardware flow chart of an example method according to one implementation in accordance with the principles and teachings of the disclosure.

FIG. 10 shows an overall block diagram for an embodiment of a minimal-area sensor for endoscope applications in which the sensor may be incorporated into the distal end of the endoscope unit.

FIGS. 11A and 11B illustrate a perspective view and a side view, respectively, of an implementation of a monolithic sensor 2900 having a plurality of pixel arrays for producing a three dimensional image in accordance with the teachings and principles of the disclosure. Such an implementation may be desirable for three dimensional image capture, wherein the two pixel arrays 2902 and 2904 may be offset during use. In another implementation, a first pixel array 2902 and a second pixel array 2904 may be dedicated to receiving a predetermined range of wave lengths of electromagnetic radiation, wherein the first pixel array is dedicated to a different range of wave length electromagnetic radiation than the second pixel array.

Figure 12A:
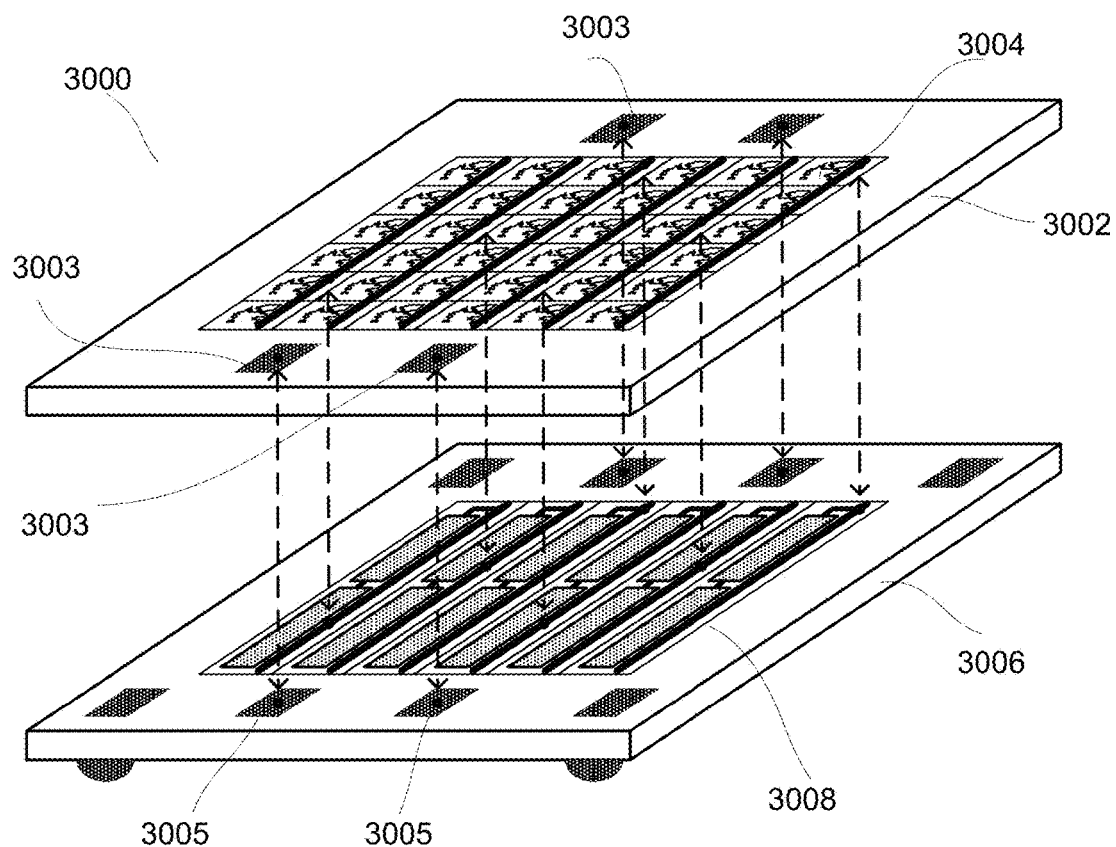
FIGS. 12A and 12B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 12B:
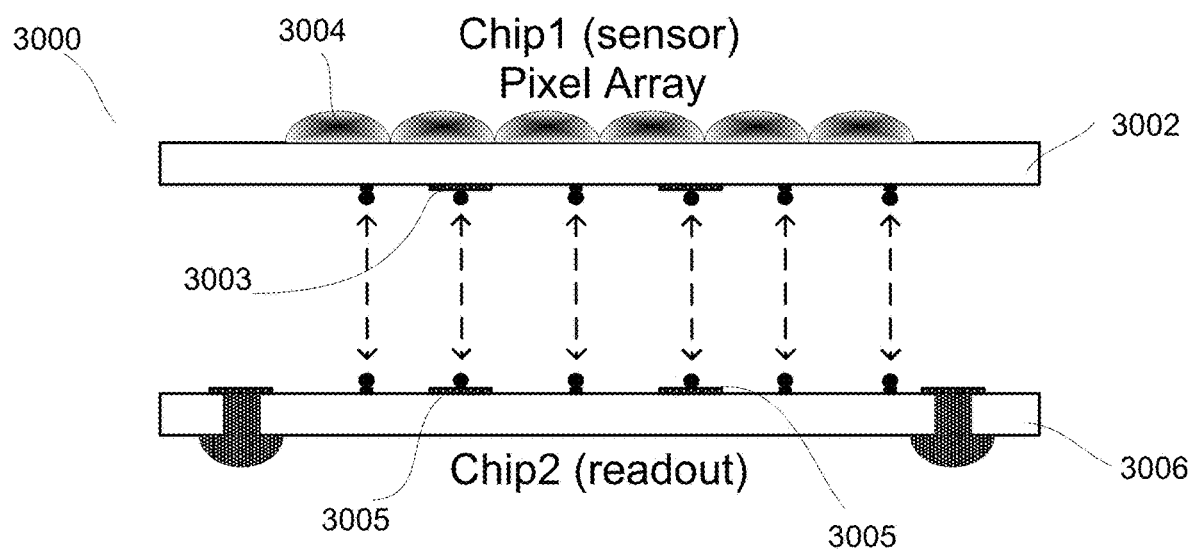

FIGS. 12A and 12B illustrate a perspective view and a side view, respectively, of an implementation of an imaging sensor 3000 built on a plurality of substrates. As illustrated, a plurality of pixel columns 3004 forming the pixel array are located on the first substrate 3002 and a plurality of circuit columns 3008 are located on a second substrate 3006. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 3002 of the two substrates/chips may be processed using an image CMOS process. The first substrate/chip 3002 may be comprised either of a pixel array exclusively or a pixel array surrounded by limited circuitry. The second or subsequent substrate/chip 3006 may be processed using any process, and does not have to be from an image CMOS process. The second substrate/chip 3006 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 3002 may be stacked with the second or subsequent substrate/chip 3006 using any three-dimensional technique. The second substrate/chip 3006 may support most, or a majority, of the circuitry that would have otherwise been implemented in the first image CMOS chip 3002 (if implemented on a monolithic substrate/chip) as peripheral circuits and therefore have increased the overall system area while keeping the pixel array size constant and optimized to the fullest extent possible. The electrical connection between the two substrates/chips may be done through interconnects 3003 and 3005, which may be wirebonds, bump and/or TSV (Through Silicon Via).

FIGS. 13A and 13B illustrate a perspective view and a side view, respectively, of an implementation of an imaging sensor 3100 having a plurality of pixel arrays for producing a three dimensional image. The three dimensional image sensor may be built on a plurality of substrates and may comprise the plurality of pixel arrays and other associated circuitry, wherein a plurality of pixel columns 3104a forming the first pixel array and a plurality of pixel columns 3104b forming a second pixel array are located on respective substrates 3102a and 3102b, respectively, and a plurality of circuit columns 3108a and 3108b are located on a separate substrate 3106. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

An embodiment of an endoscope for use in a closed light environment may comprise: an endoscope body providing a hand holding structure, a lumen attached by a lumen base at a first end of the body, a tip portion of the lumen opposite of the lumen base of the, a lens that may be disposed at the most distal portion of the tip portion, an imaging sensor that may be disposed near the tip portion of the lumen comprising: an array of pixels for sensing electromagnetic radiation; wherein the pixel array may have active pixels and optical black pixels for calibrating output from said pixel array; wherein the optical black pixels may be organized in columns adjacent to active pixels within the pixel array; a transfer port for transmitting data generated by the pixel array; a digitizer to convert analog pixel samples to digital numbers; a black clamp circuit for providing offset control for the data generated by the pixel array; a process that may be stored in memory for controlling the black clamp circuit; electrical connections that may be providing electrical communication between the imaging sensor and image signal processing circuitry that may be disposed remote to the imaging sensor within the endoscope body and a control unit.

An embodiment of a system for digital imaging in an ambient light deficient environment may comprise: an imaging sensor for sensing electromagnetic radiation; wherein said imaging sensor may further comprise: a pixel array having active pixels and optical black pixels for calibrating output from said pixel array; wherein the optical black pixels may be organized in columns adjacent to active pixels within the pixel array; a transfer port for transmitting data generated by the pixel array; a digitizer to convert analog pixel samples to digital numbers; a black clamp circuit for providing offset control for the data generated by the pixel array; a process that may be stored in memory of the system for controlling the black clamp circuit; an endoscope for accessing the ambient light deficient environment; a hand piece attached to said endoscope and wherein said endoscope may be maneuvered by manipulation of the hand piece; a control unit comprising a processor and wherein said control unit may be in electrical communication with the imaging sensor; and a connection cable electrically connecting the hand piece and the control unit.

Additionally, the teachings and principles of the disclosure may include any and all wavelengths of electromagnetic energy, including the visible and non-visible spectrums, such as infrared (IR), ultraviolet (UV), and X-ray.

The foregoing description has been presented for the purposes of illustration and description. It may be not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure may be not to be limited to the specific forms or arrangements of parts so described and illustrated. The scope of the disclosure may be to be defined by the claims appended hereto, any future claims submitted here and in different applications, and their equivalents.

What is claimed is:

1. A method of calibrating an image sensor, comprising:
providing an image sensor having a first optical black portion and a second optical black portion separated from each other by an active pixel portion;
sampling one or more pixels in the first optical black portion and adding the results to an accumulator;
determining, in response to sampling one or more pixels in the first optical black portion, a black level for the first optical black portion;
comparing the determined black level to a target black level by subtracting the target black level from the determined black level to determine the overall black level for the first optical black portion;
determining whether the overall black level is greater than a threshold black level, and when the overall black level is greater than the threshold black level, applying a proportional adjustment to a blackclamp voltage in the image sensor, and when the overall black level is less than the threshold black level, applying an incremental adjustment to the blackclamp voltage in the image sensor.

2. The method of calibrating the image sensor of claim 1, wherein the image sensor is a CMOS image sensor.

3. The method of calibrating the image sensor of claim 1, wherein calibrating the image sensor includes calibrating the black clamp voltage.

4. The method of calibrating the image sensor of claim 1, wherein calibrating the image sensor includes calibrating the line noise for each column of pixels in the first optical black portion.

5. The method of calibrating the image sensor of claim 1, wherein sampling the one or more pixels in the first optical black portion includes determining a median black offset measurement for each one of the one or more pixels in the first optical black portion and a plurality of other pixels proximate to the each one of the one or more pixels in the first optical black portion.

6. The method of calibrating the image sensor of claim 5, wherein the median black offset measurement for each one of the one or more pixels in the first optical black portion is averaged to provide a final line offset estimate.

7. The method of calibrating the image sensor of claim 1, further comprising:
sampling one or more pixels in the second optical black portion and adding the results to an accumulator;
determining, in response to sampling one or more pixels in the second optical black portion, a black level for the second optical black portion;
comparing the determined black level to a target black level by subtracting the target black level from the determined black level to determine the overall black level for the second optical black portion;
determining whether the overall black level for the first optical black portion and the second optical black portion is greater than a threshold black level, and when the overall black level is greater than the threshold black level, applying a proportional adjustment to a blackclamp voltage in the image sensor, and when the overall black level is less than the threshold black level, applying an incremental adjustment to the blackclamp voltage in the image sensor.

8. The method of calibrating the image sensor of claim 7, wherein sampling the one or more pixels in the second optical black portion includes determining a median black offset measurement for each one of the one or more pixels in the second optical black portion and a plurality of other pixels proximate to the each one of the one or more pixels in the first optical black portion.

9. The method of calibrating the image sensor of claim 8, wherein sampling the one or more pixels in the second optical black portion includes wrapping around a plurality of pixels at an end of the second optical black portion to a beginning of the first optical black portion.

10. The method of calibrating the image sensor of claim 9, further comprising:
averaging the median black offset measurement for each one of the one or more pixels in the second optical black portion to provide a final line offset estimate.

11. The method of calibrating the image sensor of claim 9, wherein the wrap around causes a delay equal to at least the total number of optical black pixels per analog-to-digital converter channel, per row of pixels.

12. The method of calibrating the image sensor of claim 9, wherein the total number of optical black pixels per analog-to-digital converter channel affected by the delay are ignored.

13. The method of calibrating the image sensor of claim 7, further comprising:
determining line offsets for the first optical black portion and the second optical black portion.

14. The method of calibrating the image sensor of claim 13, further comprising:
determining an overall black level by incrementally adjusting a running estimate.

15. The method of calibrating the image sensor of claim 14, further comprising updating the running estimate when the sample is divisible by a binary number ($2^q$).

16. The method of calibrating the image sensor of claim 15, wherein the updating the running estimate includes multiplying a previous estimate by $(2^q-1)/2^q$ where q is a tunable parameter.

17. The method of calibrating the image sensor of claim 7, wherein the proportional adjustment corresponds to more than one digital-to-analog converter count.

18. The method of calibrating the image sensor of claim 7, wherein the incremental adjustment corresponds to one digital-to-analog converter count.

19. The method of calibrating the image sensor of claim 7, wherein the blackclamp voltage is applied when optical black pixels from the first optical black portion or the second optical black portion are in a digital readout path for the image sensor.

20. The method of calibrating the image sensor of claim 19, wherein the blackclamp voltage applied to the optical black pixels in the digital readout path reduces line noise.

* * * * *